(12) United States Patent
Krey et al.

(10) Patent No.: US 8,735,346 B2
(45) Date of Patent: May 27, 2014

(54) HCV-DERIVED POLYPEPTIDES AND USES THEREOF

(75) Inventors: Thomas Krey, Trappes (FR); Felix A. Rey, Gif-sur-Yvette (FR); Carlos Massayuki Kikuti, Bagneux (FR); Laurence Damier-Piolle, Issy les Moulineaux (FR)

(73) Assignee: Institut Pasteur, Paris (FR)

( * ) Notice: Subject to any disclaimer, the term of this patent is extended or adjusted under 35 U.S.C. 154(b) by 35 days.

(21) Appl. No.: 13/256,786

(22) PCT Filed: Mar. 17, 2010

(86) PCT No.: PCT/IB2010/051158
§ 371 (c)(1),
(2), (4) Date: Nov. 23, 2011

(87) PCT Pub. No.: WO2010/106509
PCT Pub. Date: Sep. 23, 2010

(65) Prior Publication Data
US 2012/0088718 A1    Apr. 12, 2012

(30) Foreign Application Priority Data
Mar. 17, 2009   (CA) .................................... 2658714

(51) Int. Cl.
*A61K 38/16*   (2006.01)
*C07K 14/18*   (2006.01)
*A61P 31/14*   (2006.01)

(52) U.S. Cl.
USPC .......... 514/4.3; 530/324; 530/350; 530/389.4

(58) Field of Classification Search
None
See application file for complete search history.

(56) References Cited

FOREIGN PATENT DOCUMENTS

| WO | WO 2006/039326 A2 | 4/2006 |
| WO | WO 2008/022401 A1 | 2/2008 |
| WO | 2008/108918 A1 | 9/2008 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
McCaffrey et al., "Expression and Characterization of a Minimal Hepatitis C Virus Glycoprotein E2 Core Domain That Retains CD81 Binding," Journal of Virology, vol. 81, No. 17, pp. 9584-9590, Sep. 2007.
Drummer et al., "A Conserved Gly$^{436}$-Trp-Leu-Ala-Gly-Leu-Phe-try Motif in Hepatitis C Virus Glycoprotein E2 is a Determinant of CD81 Bniding and Viral Entry," Journal of Virology, vol. 80, No. 16, pp. 7844-7853, Aug. 2006.
Flint et al., "Characterization of Hepatitis C Virus E2 Glycoprotein Interaction with a Putative Cellular Receptor, CD81," Journal of Virology, vol. 72, No. 8, pp. 6235-6244, Aug. 1999.
Grollo et al., "Exploiting information inherent in binding sites of virus-specific antibodies: design of an HCV vaccine candidate cross-reactive with multiple gentotypes," Antiviral Therapy, vol. 11, pp. 1005-1014, Jan. 2006.
Owsianka et al., "Monoclonal Antibody AP33 Defines a Broadly Neutralizing Epitope on the Hepatitis C Virus E2 Envelope Glycoprotein," Journal of Virology, vol. 79, No. 17, pp. 11095-11104, Sep. 2005.
Krey et al., "The Disulfide Bonds in Glycoprotein E2 of Hepatitis C Virus Reveal the Tertiary Organization of the Molecule," Plos Pathogens, vol. 6, No. 2, p. e1000762, Feb. 2010.
Whidby et al., "Blocking Hepatitis C Virus Infection with Recombinant Form of Envelope Protein 2 Ectodomain," Journal of Virology, vol. 83, No. 21, pp. 11078-11089, Nov. 2009.
Fenouillet et al., "Contribution of Redox Status to Hepatitis C Virus E2 Envelope Protein Function and Antigenicity," The Journal of Biological Chemistry, vol. 283, No. 39, pp. 26340-26348, Sep. 2008.
International Search Report issued in application No. PCT/IB2010/051158 on Nov. 10, 2010.

* cited by examiner

*Primary Examiner* — Julie Ha
*Assistant Examiner* — Li Ni Komatsu
(74) *Attorney, Agent, or Firm* — Foley & Lardner LLP

(57) ABSTRACT

The present invention relates to Hepatitis C virus (HCV)-derived polypeptides and nucleic acid molecules encoding same which advantageously comprises a cd81-binding region. In this connection, the present invention specifically relates to the use of the polypeptides or nucleic acid molecules in compositions and methods for the prevention, the treatment and the diagnosis of HCV infections.

6 Claims, 7 Drawing Sheets

|         | % Alpha | % Beta | % Turn | % Unrd |
|---------|---------|--------|--------|--------|
| HCV E2  | 5.0     | 37.0   | 13.0   | 43.0   |
| Chik E1 | 4.7     | 40.5   | 12.5   | 41.0   |
| WNV E   | 5.0     | 41     | 11.5   | 40.5   |

Figure 4 ns to Hepatitis C virus (HCV)-

SEQUENCE LISTING

```
<160> NUMBER OF SEQ ID NOS: 41

<210> SEQ ID NO 1
<211> LENGTH: 95
<212> TYPE: PRT
<213> ORGANISM: Artificial sequence
<220> FEATURE:
<223> OTHER INFORMATION: Domain I of the E2 protein of the HCV H77C
      genotype 1a strain

<400> SEQUENCE: 1

Gln Asn Ile Gln Leu Ile Asn Thr Asn Gly Ser Trp His Ile Asn Ser
1               5                   10                  15

Thr Ala Leu Asn Cys Asn Glu Ser Leu Asn Thr Gly Trp Leu Ala Gly
                20                  25                  30

Leu Phe Tyr Gln His Lys Phe Asn Ser Ser Gly Ser Gly Ala Pro Thr
            35                  40                  45

Tyr Ser Trp Gly Ala Asn Asp Thr Asp Val Phe Val Leu Asn Asn Thr
        50                  55                  60

Arg Pro Pro Leu Gly Asn Trp Phe Gly Cys Thr Trp Met Asn Ser Thr
65                  70                  75                  80

Gly Phe Thr Lys Val Cys Gly Ala Pro Pro Cys Val Ile Gly Gly
                85                  90                  95

<210> SEQ ID NO 2
<211> LENGTH: 88
<212> TYPE: PRT
<213> ORGANISM: Artificial sequence
<220> FEATURE:
<223> OTHER INFORMATION: Domain I of the E2 protein of the HCV UKN2b_2.8
      genotype 2b strain

<400> SEQUENCE: 2

Ser Leu Ile Asn Thr Asn Gly Ser Trp His Ile Asn Arg Thr Ala Leu
1               5                   10                  15

Asn Cys Asn Asp Ser Leu Gln Thr Gly Phe Leu Ala Ser Leu Phe Tyr
                20                  25                  30

Val Lys Asn Phe Asn Ser Ser Gly Gln Gly Val Pro Tyr Ser Trp
            35                  40                  45

Gly Glu Asn Glu Thr Asp Val Phe Leu Leu Asn Ser Thr Arg Pro Pro
        50                  55                  60

Gln Gly Ala Trp Phe Gly Cys Thr Trp Met Asn Gly Thr Gly Phe Thr
65                  70                  75                  80

Lys Thr Cys Gly Ala Pro Pro Cys
                85
```

-continued

```
<210> SEQ ID NO 3
<211> LENGTH: 67
<212> TYPE: PRT
<213> ORGANISM: Artificial sequence
<220> FEATURE:
<223> OTHER INFORMATION: Domain III of the E2 protein of the HCV H77C
      genotype 1a strain

<400> SEQUENCE: 3

Cys Pro Thr Asp Cys Phe Arg Lys His Pro Glu Ala Thr Tyr Ser Arg
1               5                   10                  15

Cys Gly Ser Gly Pro Trp Ile Thr Pro Arg Cys Met

Ser Gly Pro Trp Ile Thr Pro Arg Cys Met Val Asp Tyr Pro Tyr Arg
            115                 120                 125

Leu Trp His Tyr Pro Cys Thr Ile Asn Tyr Thr Ile Phe Lys Val Arg
        130                 135                 140

Met Tyr Val Gly Gly Val Glu His Arg Leu Glu Ala Ala Cys Asn Trp
145                 150                 155                 160

Thr Arg Gly Glu Arg
                165

<210> SEQ ID NO 6
<211> LENGTH: 173
<212> TYPE: PRT
<213> ORGANISM: Artificial sequence
<220> FEATURE:
<223> OTHER INFORMATION: Domains I+III with linker of the E2 protein of
      the HCV H77C genotype 1a strain

<400> SEQUENCE: 6

Gln Asn Ile Gln Leu Ile Asn Thr Asn Gly Ser Trp His Ile Asn Ser
1               5                   10                  15

Thr Ala Leu Asn Cys Asn Glu Ser Leu Asn Thr Gly Trp Leu Ala Gly
            20                  25                  30

Leu Phe Tyr Gln His Lys Phe Asn Ser Ser Gly Ser Gly Ala Pro Thr
        35                  40                  45

Tyr Ser Trp Gly Ala Asn Asp Thr Asp Val Phe Val Leu Asn Asn Thr
    50                  55                  60

Arg Pro Pro Leu Gly Asn Trp Phe Gly Cys Thr Trp Met Asn Ser Thr
65                  70                  75                  80

Gly Phe Thr Lys Val Cys Gly Ala Pro Pro Cys Val Ile Gly Gly Val
                85                  90                  95

Gly Asn Asn Thr Leu Leu Cys Pro Thr Asp Cys Phe Arg Lys His Pro
            100                 105                 110

Glu Ala Thr Tyr Ser Arg Cys Gly Ser Gly Pro Trp Ile Thr Pro Arg
        115                 120                 125

Cys Met Val Asp Tyr Pro Tyr Arg Leu Trp His Tyr Pro Cys Thr Ile
    130                 135                 140

Asn Tyr Thr Ile Phe Lys Val Arg Met Tyr Val Gly Gly Val Glu His
145                 150                 155                 160

Arg Leu Glu Ala Ala Cys Asn Trp Thr Arg Gly Glu Arg
                165                 170

<210> SEQ ID NO 7
<211> LENGTH: 165
<212> TYPE: PRT
<213> ORGANISM: Artificial sequence
<220> FEATURE:
<223> OTHER INFORMATION: Domains I+III with linker of the E2 protein of
      the HCV UKN2b_2.8 genotype 2b strain

<400> SEQUENCE: 7

Ser Leu Ile Asn Thr Asn Gly Ser Trp His Ile Asn Arg Thr Ala Leu
1               5                   10                  15

Asn Cys Asn Asp Ser Leu Gln Thr Gly Phe Leu Ala Ser Leu Phe Tyr
            20                  25                  30

Val Lys Asn Phe Asn Ser Ser Gly Gln Gly Val Pro Thr Tyr Ser Trp
        35                  40                  45

Gly Glu Asn Glu Thr Asp Val Phe Leu Leu Asn Ser Thr Arg Pro Pro
    50                  55                  60

Gln Gly Ala Trp Phe Gly Cys Thr Trp Met Asn Gly Thr Gly Phe Thr

```
                65                  70                  75                  80
Lys Thr Cys Gly Ala Pro Pro Cys Arg Ile Arg Lys Asp His Asn Ser
                    85                  90                  95
Thr Leu Asp Leu Leu Cys Pro Thr Asp Cys Phe Arg Lys His Pro Asp
                    100                 105                 110
Thr Thr Tyr Leu Lys Cys Gly Ala Gly Pro Trp Leu Thr Pro Arg Cys
            115                 120                 125
Leu Val Asp Tyr Pro Tyr Arg Leu Trp His Tyr Pro Cys Thr Val Asn
        130                 135                 140
Phe Thr Ile Phe Lys Val Arg Met Tyr Val Gly Gly Val Glu His Arg
145                 150                 155                 160

Leu Asn Ala Ala Cys
                165

<210> SEQ ID NO 8
<211> LENGTH: 285
<212> TYPE: DNA
<213> ORGANISM: Artificial sequence
<220> FEATURE:
<223> OTHER INFORMATION: Coding sequence of domain I of the E2 protein
      of the HCV H77C genotype 1a strain

<400> SEQUENCE: 8
caaaatatcc agctcatcaa cacaaatggg agctggcaca taaactccac ggccctaaac        60
tgcaacgaga gtctgaatac tggctggctg ccggtttgt tctaccaaca caagttcaac       120
tcctcgggca gcggcgcccc gacttacagt tggggcgcca acgatacgga cgttttcgtg       180
ctgaacaata cacgcccccc cctaggcaac tggtttggat gcacgtggat gaacagtaca       240
ggattcacta agtgtgtgg cgctcctccg tgcgtgatcg gtggc                       285

<210> SEQ ID NO 9
<211> LENGTH: 270
<212> TYPE: DNA
<213> ORGANISM: Artificial sequence
<220> FEATURE:
<223> OTHER INFORMATION: Coding sequence of domain I of the E2 protein
      of the HCV UKN2b_2.8 genotype 2b strain

<400> SEQUENCE: 9
agtctgatca ataccaacgg atcatggcac atcaaccgca cggctctcaa ctgcaatgat        60
agtctgcaga caggctttct ggcaagtctg ttttacgtga agaacttcaa cagttcggga       120
cagggtgtgc caacgtactc ctggggagag aacgagacag acgttttcct tctgaatagc       180
acccgtccgc cccaaggagc ctggtttggt tgtacttgga tgaacggaac cggttttacc       240
aagacctgcg gtgcaccgcc ctgtggagcc                                       270

<210> SEQ ID NO 10
<211> LENGTH: 201
<212> TYPE: DNA
<213> ORGANISM: Artificial sequence
<220> FEATURE:
<223> OTHER INFORMATION: Coding sequence of domain III of the E2
      protein of the HCV H77C genotype 1a strain

<400> SEQUENCE: 10
tgcccaactg attgcttccg taagcatcca gaagcaacct actcccgttg cggcagtggg        60
ccctggatta ctccccgttg catggtcgac tatccataca ggctgtggca ctacccgtgc       120
actattaact ataccatctt caaggtgagg atgtatgttg aggcgtggaa gcatcgtctg       180
gaggccgcct gcaattggac g                                                201
```

<210> SEQ ID NO 11
<211> LENGTH: 192
<212> TYPE: DNA
<213> ORGANISM: Artificial sequence
<220> FEATURE:
<223> OTHER INFORMATION: Coding sequence of domain III of the E2 protein
      of the HCV UKN2b_2.8 genotype 2b strain

<400> SEQUENCE: 11
tgccccacag actgcttcag aaagcaccca gataccacgt atttgaagtg cggcgcggga      60
ccatggctca cgcctaggtg tttggtggat tatccctata gactttggca ctatccatgc     120
acggttaatt tcaccatctt caaggtgcgc atgtacgtag gcggtgtgga acaccgattg     180
aacgcggctt gt                                                        192

<210> SEQ ID NO 12
<211> LENGTH: 495
<212> TYPE: DNA
<213> ORGANISM: Artificial sequence
<220> FEATURE:
<223> OTHER INFORMATION: Coding sequence of domains I+III without
      linker of the E2 protein of the HCV H77C genotype 1a strain

<400> SEQUENCE: 12
caaaatatcc agctcatcaa cacaaatggg agctggcaca taaactccac ggccctaaac      60
tgcaacgaga gtctgaatac tggctggctg ccggtttgt tctaccaaca caagttcaac     120
tcctcgggca gcggcgcccc gacttacagt tggggcgcca acgatacgga cgttttcgtg    180
ctgaacaata cacgcccccc cctaggcaac tggtttggat gcacgtggat gaacagtaca    240
ggattcacta aagtgtgtgg cgctcctccg tgcgtgccg ctgcccaac tgattgcttc      300 cgtaagcatc cagaagcaac ctactcccgt gcggcagtg ggccctggat tactccccgt    360
tgcatggtcg actatccata caggctgtgg cactacccgt gcactattaa ctataccatc    420
ttcaaggtga ggatgtatgt tggaggcgtg gagcatcgtc tggaggccgc ctgcaattgg    480
acgcgcggcg agcgg                                                    495

<210> SEQ ID NO 13
<211> LENGTH: 519
<212> TYPE: DNA
<213> ORGANISM: Artificial sequence
<220> FEATURE:
<223> OTHER INFORMATION: Coding sequence of domains I+III with linker
      of the E2 protein of the HCV H77C genotype 1a strain

<400> SEQUENCE: 13
caaaatatcc agctcatcaa cacaaatggg agctggcaca taaactccac ggccctaaac      60
tgcaacgaga gtctgaatac tggctggctg ccggtttgt tctaccaaca caagttcaac     120
tcctcgggca gcggcgcccc gacttacagt tggggcgcca acgatacgga cgttttcgtg    180
ctgaacaata cacgcccccc cctaggcaac tggtttggat gcacgtggat gaacagtaca    240
ggattcacta aagtgtgtgg cgctcctccg tgcgtgatcg gtggcgtcgg caacaatact    300
ctcttatgcc caactgattg cttccgtaag catccagaag caacctactc ccgttgcggc    360
agtgggccct ggattactcc ccgttgcatg gtcgactatc catacaggct gtggcactac    420
ccgtgcacta ttaactatac catcttcaag gtgaggatgt atgttggagg cgtggagcat    480
cgtctggagg ccgcctgcaa ttggacgcgc ggcgagcgg                          519

<210> SEQ ID NO 14

<211> LENGTH: 495
<212> TYPE: DNA
<213> ORGANISM: Artificial sequence
<220> FEATURE:
<223> OTHER INFORMATION: Coding sequence of domains I+III with linker of the E2 protein of the HCV UKN2b_2.8 genotype 2b strain

<400> SEQUENCE: 14

```
agtctgatca ataccaacgg atcatggcac atcaaccgca cggctctcaa ctgcaatgat     60
agtctgcaga caggctttct ggcaagtctg ttttacgtga agaacttcaa cagttcggga    120
cagggtgtgc caacgtactc ctggggagag aacgagacag acgttttcct tctgaatagc    180
acccgtccgc cccaaggagc ctggtttggt tgtacttgga tgaacggaac cggttttacc    240
aagacctgcg gtgcaccgcc ctgtcggata aggaaggacc acaactctac gctcgatttg    300
ctctgcccca cagactgctt cagaaagcac ccagatacca cgtatttgaa gtgcggcgcg    360
ggaccatggc tcacgcctag gtgtttggtg gattatccct atagactttg gcactatcca    420
tgcacggtta atttcaccat cttcaaggtg cgcatgtacg taggcggtgt ggaacaccga    480
ttgaacgcgg cttgt                                                     495
```

<210> SEQ ID NO 15
<211> LENGTH: 332
<212> TYPE: PRT
<213> ORGANISM: Artificial sequence
<220> FEATURE:
<223> OTHER INFORMATION: sE2,715 from HCV H77 strain

<400> SEQUENCE: 15

```
Glu Thr His Val Thr Gly Gly Asn Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys Tyr Pro Glu
        195                 200                 205

Ala Thr Tyr Ser Arg Cys Gly Ser Gly Pro Arg Ile Thr Pro Arg Cys
    210                 215                 220

Met Val Asp Tyr Pro Tyr Arg Leu Trp His Tyr Pro Cys Thr Ile Asn

```
                225                 230                 235                 240
Tyr Thr Ile Phe Lys Val Arg Met Tyr Val Gly Gly Val Glu His Arg
                    245                 250                 255

Leu Glu Ala Ala Cys Asn Trp Thr Arg Gly Glu Arg Cys Asp Leu Glu
                260                 265                 270

Asp Arg Asp Arg Ser Glu Leu Ser Pro Leu Leu Leu Ser Thr Thr Gln
            275                 280                 285

Trp Gln Val Leu Pro Cys Ser Phe Thr Thr Leu Pro Ala Leu Ser Thr
        290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys
                325                 330

<210> SEQ ID NO 16
<211> LENGTH: 336
<212> TYPE: PRT
<213> ORGANISM: Artificial sequence
<220> FEATURE:
<223> OTHER INFORMATION: sE2,715 from HCV JFH-1 strain

<400> SEQUENCE: 16

Gly Thr Thr Thr Val Gly Gly Ala Val Ala Arg Ser Thr Asn Val Ile
1               5                   10                  15

Ala Gly Val Phe Ser His Gly Pro Gln Gln Asn Ile Gln Leu Ile Asn
                20                  25                  30

Thr Asn Gly Ser Trp His Ile Asn Arg Thr Ala Leu Asn Cys Asn Asp
            35                  40                  45

Ser Leu Asn Thr Gly Phe Leu Ala Ala Leu Phe Tyr Thr Asn Arg Phe
50                  55                  60

Asn Ser Ser Gly Cys Pro Gly Arg Leu Ser Ala Cys Arg Asn Ile Glu
65                  70                  75                  80

Ala Phe Arg Ile Gly Trp Gly Thr Leu Gln Tyr Glu Asp Asn Val Thr
                85                  90                  95

Asn Pro Glu Asp Met Arg Pro Tyr Cys Trp His Tyr Pro Pro Lys Pro
            100                 105                 110

Cys Gly Val Val Pro Ala Arg Ser Val Cys Gly Pro Val Tyr Cys Phe
        115                 120                 125

Thr Pro Ser Pro Val Val Val Gly Thr Thr Asp Arg Arg Gly Val Pro
130                 135                 140

Thr Tyr Thr Trp Gly Glu Asn Glu Thr Asp Val Phe Leu Leu Asn Ser
145                 150                 155                 160

Thr Arg Pro Pro Gln Gly Ser Trp Phe Gly Cys Thr Trp Met Asn Ser
                165                 170                 175

Thr Gly Phe Thr Lys Thr Cys Gly Ala Pro Pro Cys Arg Thr Arg Ala
            180                 185                 190

Asp Phe Asn Ala Ser Thr Asp Leu Leu Cys Pro Thr Asp Cys Phe Arg
        195                 200                 205

Lys His Pro Asp Ala Thr Tyr Ile Lys Cys Gly Ser Gly Pro Trp Leu
    210                 215                 220

Thr Pro Lys Cys Leu Val His Tyr Pro Tyr Arg Leu Trp His Tyr Pro
225                 230                 235                 240

Cys Thr Val Asn Phe Thr Ile Phe Lys Ile Arg Met Tyr Val Gly Gly
                245                 250                 255

Val Glu His Arg Leu Thr Ala Ala Cys Asn Phe Thr Arg Gly Asp Arg
            260                 265                 270
```

```
Cys Asp Leu Glu Asp Arg Asp Arg Ser Gln Leu Ser Pro Leu Leu His
            275                 280                 285

Ser Thr Thr Glu Trp Ala Ile Leu Pro Cys Thr Tyr Ser Asp Leu Pro
    290                 295                 300

Ala Leu Ser Thr Gly Leu Leu His Leu His Gln Asn Ile Val Asp Val
305                 310                 315                 320

Gln Tyr Met Tyr Gly Leu Ser Pro Ala Ile Thr Lys Tyr Val Val Arg
                325                 330                 335

<210> SEQ ID NO 17
<211> LENGTH: 336
<212> TYPE: PRT
<213> ORGANISM: Artificial sequence
<220> FEATURE:
<223> OTHER INFORMATION: sE2,715 from HCV UKN2b_2.8 strain

<400> SEQUENCE: 17

His Thr Arg Leu Ile Gly Ser Val Ala Gly Arg Asn Thr Asp Thr Leu
1               5                   10                  15

Arg Ser Leu Phe Ala Thr Gly Ala Gln Gln Lys Ile Ser Leu Ile Asn
            20                  25                  30

Thr Asn Gly Ser Trp His Ile Asn Arg Thr Ala Leu Asn Cys Asn Asp
        35                  40                  45

Ser Leu Gln Thr Gly Phe Leu Ala Ser Leu Phe Tyr Val Lys Asn Phe
    50                  55                  60

Asn Ser Ser Gly Cys Pro Glu Arg Met Ser Ser Cys Arg Glu Leu Asp
65                  70                  75                  80

Asp Phe Arg Ile Gly Trp Gly Thr Leu Glu Tyr Glu Thr Asn Ala Thr
                85                  90                  95

Asn Asp Glu Asp Met Arg Pro Tyr Cys Trp His Tyr Pro Arg Pro
            100                 105                 110

Cys Gly Ile Val Ser Ala Arg Thr Val Cys Gly Pro Val Tyr Cys Phe
        115                 120                 125

Thr Pro Ser Pro Val Val Gly Thr Thr Asp Arg Gln Gly Val Pro
    130                 135                 140

Thr Tyr Ser Trp Gly Glu Asn Glu Thr Asp Val Phe Leu Leu Asn Ser
145                 150                 155                 160

Thr Arg Pro Pro Gln Gly Ala Trp Phe Gly Cys Thr Trp Met Asn Gly
                165                 170                 175

Thr Gly Phe Thr Lys Thr Cys Gly Ala Pro Pro Cys Arg Ile Arg Lys
            180                 185                 190

Asp His Asn Ser Thr Leu Asp Leu Leu Cys Pro Thr Asp Cys Phe Arg
        195                 200                 205

Lys His Pro Asp Thr Thr Tyr Leu Lys Cys Gly Ala Gly Pro Trp Leu
    210                 215                 220

Thr Pro Arg Cys Leu Val Asp Tyr Pro Tyr Arg Leu Trp His Tyr Pro
225                 230                 235                 240

Cys Thr Val Asn Phe Thr Ile Phe Lys Val Arg Met Tyr Val Gly Gly
                245                 250                 255

Val Glu His Arg Leu Asn Ala Ala Cys Asn Phe Thr Arg Gly Asp Arg
            260                 265                 270

Cys Arg Leu Glu Asp Arg Asp Arg Gly Gln Gln Ser Pro Leu Leu His
        275                 280                 285

Ser Thr Thr Glu Trp Ala Val Leu Pro Cys Ser Phe Ser Asp Leu Pro
    290                 295                 300
```

```
Ala Leu Ser Thr Gly Leu Leu His Leu His Gln Asn Ile Val Asp Val
305                 310                 315                 320

Gln Tyr Leu Tyr Gly Leu Thr Pro Ala Ile Thr Arg Tyr Ile Val Lys
            325                 330                 335
```

<210> SEQ ID NO 18
<211> LENGTH: 12
<212> TYPE: PRT
<213> ORGANISM: Artificial sequence
<220> FEATURE:
<223> OTHER INFORMATION: Linker

<400> SEQUENCE: 18

```
Gly Gly Ser Gly Gly Ser Gly Gly Ser Gly Gly Ser
1               5                   10
```

<210> SEQ ID NO 19
<211> LENGTH: 35
<212> TYPE: PRT
<213> ORGANISM: Artificial sequence
<220> FEATURE:
<223> OTHER INFORMATION: Linker and cleavage region

<400> SEQUENCE: 19

```
Asp Asp Asp Asp Lys Ala Gly Trp Ser His Pro Gln Phe Glu Lys Gly
1               5                   10                  15

Gly Gly Ser Gly Gly Gly Ser Gly Gly Ser Trp Ser His Pro Gln
            20                  25                  30

Phe Glu Lys
        35
```

<210> SEQ ID NO 20
<211> LENGTH: 9
<212> TYPE: PRT
<213> ORGANISM: Artificial sequence
<220> FEATURE:
<223> OTHER INFORMATION: Proteolytic fragment from HCV E2

<400> SEQUENCE: 20

```
Phe Asp Ser Ser Gly Cys Pro Gly Arg
1               5
```

<210> SEQ ID NO 21
<211> LENGTH: 5
<212> TYPE: PRT
<213> ORGANISM: Artificial sequence
<220> FEATURE:
<223> OTHER INFORMATION: Proteolytic fragment from HCV E2

<400> SEQUENCE: 21

```
Leu Ser Ala Cys Arg
1               5
```

<210> SEQ ID NO 22
<211> LENGTH: 36
<212> TYPE: PRT
<213> ORGANISM: Artificial sequence
<220> FEATURE:
<223> OTHER INFORMATION: Proteolytic fragment from HCV E2

<400> SEQUENCE: 22

```
Ile Gly Trp Gly Thr Leu Gln Tyr Glu Asp Asp Val Thr Asn Pro Glu
1               5                   10                  15

Asp Met Arg Pro Tyr Cys Trp His Tyr Pro Pro Lys Pro Cys Gly Val
            20                  25                  30
```

```
Val Pro Ala Arg
        35

<210> SEQ ID NO 23
<211> LENGTH: 22
<212> TYPE: PRT
<213> ORGANISM: Artificial sequence
<220> FEATURE:
<223> OTHER INFORMATION: Proteolytic fragment from HCV E2

<400> SEQUENCE: 23

Ser Val Cys Gly Pro Val Tyr Cys Phe Thr Pro Ser Pro Val Val Val
1               5                   10                  15

Gly Thr Thr Asp Arg Arg
            20

<210> SEQ ID NO 24
<211> LENGTH: 17
<212> TYPE: PRT
<213> ORGANISM: Artificial sequence
<220> FEATURE:
<223> OTHER INFORMATION: Proteolytic fragment from HCV E2

<400> SEQUENCE: 24

Ala Asp Phe Asp Ala Ser Thr Asp Leu Leu Cys Pro Thr Asp Cys Phe
1               5                   10                  15

Arg

<210> SEQ ID NO 25
<211> LENGTH: 8
<212> TYPE: PRT
<213> ORGANISM: Artificial sequence
<220> FEATURE:
<223> OTHER INFORMATION: Proteolytic fragment from HCV E2

<400> SEQUENCE: 25

Cys Leu Val His Tyr Pro Tyr Arg
1               5

<210> SEQ ID NO 26
<211> LENGTH: 9
<212> TYPE: PRT
<213> ORGANISM: Artificial sequence
<220> FEATURE:
<223> OTHER INFORMATION: Proteolytic fragment from HCV E2

<400> SEQUENCE: 26

Leu Thr Ala Ala Cys Asn Phe Thr Arg
1               5

<210> SEQ ID NO 27
<211> LENGTH: 21
<212> TYPE: PRT
<213> ORGANISM: Artificial sequence
<220> FEATURE:
<223> OTHER INFORMATION: Proteolytic fragment from HCV E2

<400> SEQUENCE: 27

Thr Ala Leu Asn Cys Asp Asp Ser Leu Gln Thr Gly Phe Leu Ala Ser
1               5                   10                  15

Leu Phe Tyr Val Lys
            20

<210> SEQ ID NO 28
<211> LENGTH: 36
<212> TYPE: PRT
```

```
<213> ORGANISM: Artificial sequence
<220> FEATURE:
<223> OTHER INFORMATION: Proteolytic fragment from HCV E2

<400> SEQUENCE: 28

Ile Gly Trp Gly Thr Leu Glu Tyr Glu Thr Asp Ala Thr Asn Asp Glu
1               5                   10                  15

Asp Met Arg Pro Tyr Cys Trp His Tyr Pro Pro Arg Pro Cys Gly Ile
                20                  25                  30

Val Ser Ala Arg
            35

<210> SEQ ID NO 29
<211> LENGTH: 21
<212> TYPE: PRT
<213> ORGANISM: Artificial sequence
<220> FEATURE:
<223> OTHER INFORMATION: Proteolytic fragment from HCV E2

<400> SEQUENCE: 29

Thr Val Cys Gly Pro Val Tyr Cys Phe Thr Pro Ser Pro Val Val Val
1               5                   10                  15

Gly Thr Thr Asp Arg
            20

<210> SEQ ID NO 30
<211> LENGTH: 40
<212> TYPE: PRT
<213> ORGANISM: Artificial sequence
<220> FEATURE:
<223> OTHER INFORMATION: Proteolytic fragment from HCV E2

<400> SEQUENCE: 30

Gln Gly Val Pro Thr Tyr Ser Trp Gly Glu Asp Glu Thr Asp Val Phe
1               5                   10                  15

Leu Leu Asp Ser Thr Arg Pro Pro Gln Gly Ala Trp Phe Gly Cys Thr
                20                  25                  30

Trp Met Asp Gly Thr Gly Phe Thr
            35                  40

<210> SEQ ID NO 31
<211> LENGTH: 16
<212> TYPE: PRT
<213> ORGANISM: Artificial sequence
<220> FEATURE:
<223> OTHER INFORMATION: Proteolytic fragment from HCV E2

<400> SEQUENCE: 31

Asp His Asp Ser Thr Leu Asp Leu Leu Cys Pro Thr Asp Cys Phe Arg
1               5                   10                  15

<210> SEQ ID NO 32
<211> LENGTH: 8
<212> TYPE: PRT
<213> ORGANISM: Artificial sequence
<220> FEATURE:
<223> OTHER INFORMATION: Proteolytic fragment from HCV E2

<400> SEQUENCE: 32

Cys Leu Val Asp Tyr Pro Tyr Arg
1               5

<210> SEQ ID NO 33
<211> LENGTH: 9
<212> TYPE: PRT
```

```
<213> ORGANISM: Artificial sequence
<220> FEATURE:
<223> OTHER INFORMATION: Proteolytic fragment from HCV E2

<400> SEQUENCE: 33

Leu Asn Ala Ala Cys Asp Phe Thr Arg
1               5

<210> SEQ ID NO 34
<211> LENGTH: 9
<212> TYPE: PRT
<213> ORGANISM: Artificial sequence
<220> FEATURE:
<223> OTHER INFORMATION: Proteolytic fragment from HCV E2

<400> SEQUENCE: 34

Phe Asp Ser Ser Gly Cys Pro Glu Arg
1               5

<210> SEQ ID NO 35
<211> LENGTH: 5
<212> TYPE: PRT
<213> ORGANISM: Artificial sequence
<220> FEATURE:
<223> OTHER INFORMATION: Proteolytic fragment from HCV E2

<400> SEQUENCE: 35

Leu Ala Ser Cys Arg
1               5

<210> SEQ ID NO 36
<211> LENGTH: 39
<212> TYPE: PRT
<213> ORGANISM: Artificial sequence
<220> FEATURE:
<223> OTHER INFORMATION: Proteolytic fragment from HCV E2

<400> SEQUENCE: 36

Leu Thr Asp Phe Ala Gln Gly Trp Gly Pro Ile Ser Tyr Ala Asp Gly
1               5                   10                  15

Ser Gly Leu Asp Glu Arg Pro Tyr Cys Trp His Tyr Pro Pro Arg Pro
            20                  25                  30

Cys Gly Ile Val Pro Ala Lys
        35

<210> SEQ ID NO 37
<211> LENGTH: 25
<212> TYPE: PRT
<213> ORGANISM: Artificial sequence
<220> FEATURE:
<223> OTHER INFORMATION: Proteolytic fragment from HCV E2

<400> SEQUENCE: 37

Val Cys Gly Ala Pro Pro Cys Val Ile Gly Gly Val Gly Asp Asn Thr
1               5                   10                  15

Leu Leu Cys Pro Thr Asp Cys Phe Arg
            20                  25

<210> SEQ ID NO 38
<211> LENGTH: 8
<212> TYPE: PRT
<213> ORGANISM: Artificial sequence
<220> FEATURE:
<223> OTHER INFORMATION: Proteolytic fragment from HCV E2

<400> SEQUENCE: 38
```

-continued

```
Cys Met Val Asp Tyr Pro Tyr Arg
1               5

<210> SEQ ID NO 39
<211> LENGTH: 9
<212> TYPE: PRT
<213> ORGANISM: Artificial sequence
<220> FEATURE:
<223> OTHER INFORMATION: Proteolytic fragment from HCV E2

<400> SEQUENCE: 39

Leu Glu Ala Ala Cys Asp Trp Thr Arg
1               5

<210> SEQ ID NO 40
<211> LENGTH: 8
<212> TYPE: PRT
<213> ORGANISM: Artificial sequence
<220> FEATURE:
<223> OTHER INFORMATION: Proteolytic fragment from HCV E2

<400> SEQUENCE: 40

Cys Asp Leu Glu Asp Arg Asp Arg
1               5

<210> SEQ ID NO 41
<211> LENGTH: 30
<212> TYPE: PRT
<213> ORGANISM: Artificial sequence
<220> FEATURE:
<223> OTHER INFORMATION: Proteolytic fragment from HCV E2
<220> FEATURE:
<221> NAME/KEY: MISC_FEATURE
<222> LOCATION: (21)..(21)
<223> OTHER INFORMATION: represents several amino acids

<400> SEQUENCE: 41

Ser Glu Leu Ser Pro Leu Leu Leu Ser Thr Thr Gln Trp Gln Val Leu
1               5                   10                  15

Pro Cys Ser Phe Xaa Ser Ser Ile Ala Ser Trp Ala Ile Lys
            20                  25                  30
```

HCV-DERIVED POLYPEPTIDES AND USES THEREOF

This application is a national phase application under 35 U.S.C. 371 of International Application No. PCT/IB2010/051158 filed Mar. 17, 2010, which claims priority to Canadian Application No. 2,658,714 filed Mar. 17, 2009.

FIELD OF THE INVENTION

The present invention relates to Hepatitis C virus (HCV)-derived polypeptides and nucleic acid molecules encoding same which advantageously comprises a cd81-binding region. In this connection, the present invention specifically relates to the use of the polypeptides or nucleic acid molecules in compositions and methods for the prevention, the treatment and the diagnosis of HCV infections.

BACKGROUND OF THE INVENTION

More than 170 million people worldwide are infected with the Hepatitis C Virus (HCV), a major human pathogen against which there is currently no vaccine and no sufficiently effective and tolerable therapeutic treatment available. In most cases, the infection causes chronic liver disease that often develops into cirrhosis and hepatocellular carcinoma. HCV is a small enveloped virus in the Hepacivirus is genus within the Flaviviridae family of positive-strand RNA viruses [2]. The viral genome is a messenger RNA of 9.5 kilobases, containing a single long open reading frame which is translated into a precursor polyprotein of ~3010 amino acids. Maturation of the precursor into the individual viral proteins is carried out by cellular and viral proteases and takes place both co- and post-translationally [3]. The structural proteins are derived from the N-terminal portion of the precursor, and include the core (C) protein and the envelope glycoproteins, E1 and E2, arranged in this order from the N-terminus of the polyprotein.

Circulating HCV virions are associated with cellular components, in particular low- and very low-density lipoproteins (LDL and VLDL) [4], which results in heterogeneous infectious particles of low buoyant density. The virus targets essentially human hepatocytes, the entry process into which is not fully understood. A number of cellular entry factors (or putative receptors) have been identified, including the tetraspanins CD81 [5], Claudins 1, 6 and 9 [6,7], occludin [8], the scavenger receptor B1 (SR-B1) [9], the LDL receptor [10], and glycosaminoglycans (GAGs) [11]. The current data suggest that several of these cellular factors are recruited sequentially for virus entry [12], however the precise order and timing of the relevant interactions is not fully understood. The major players of the virion are the envelope proteins E1 and E2, but their individual specific roles during entry have not been experimentally demonstrated. It has been shown that after initial attachment to glycosaminoglycans [11] E2 binds to SR-BI, an interaction involving a segment called "hypervariable region 1" (HVR1) at the N-terminus of E2 [9, 12, 13]. Furthermore, E2 also interacts with CD81, the binding site of which includes three discontinuous stretches in E2 that are distant in the primary structure [14-17]. It has been reported that CD81 and SR-BI act cooperatively to initiate the entry process [18]. The HCV virion is then internalized by receptor-mediated endocytosis via clathrin-coated vesicles [19,20]. The low pH environment of the endosome is believed to trigger a fusogenic conformational change in the envelope proteins, inducing fusion of the viral and endosomal membranes and the release of the genomic RNA into the cytoplasm of the target cell.

The 3D organization of the HCV envelope has been poorly studied, essentially because of the difficulties in producing enough material for the relevant structural analyses. Several properties of the HCV envelope glycoproteins as well as of viral particles have therefore been inferred by extrapolation from better-studied members of the Flaviviridae family, namely the viruses forming the flavivirus genus. In spite of the lack of sequence conservation in the structural protein region, the members of the different genera within this family have the same genomic organization as HCV, encoding the structural proteins in the same order in the N-terminal portion of the precursor polyprotein. Moreover, the organization of the structural genes in HCV is also similar to members of the related Togaviridae family of small enveloped, positive-strand RNA viruses, comprising the alphaviruses genus for which structural studies are also available. Similar to HCV, the envelope proteins of viruses belonging to these families fold as a heterodimer in the ER of the infected cell and in both cases the first envelope protein has been shown to play a chaperone role in the folding of the second one [21,22].

The envelope proteins of flavi- and alphaviruses appear to have diverged from a distant common ancestor—as suggested by the crystal structure of their corresponding membrane fusion proteins, E and E1, respectively, which display the same 3D fold and are the prototype of the class II membrane fusogenic proteins. The acid pH induced fusogenic conformational changes of flavivirus E and alphavirus E1, have both been structurally characterized [23-25]. These structural studies have provided insight into the process of membrane fusion induced by the beta-rich class II fusion proteins, revealing important mechanistic similarities to that of the predominantly alpha-helical "class I" proteins (reviewed in [26]). It is widely believed that viruses belonging to other genera within these families—including HCV—are likely to code for class II fusion proteins as well. The tertiary structure of class II proteins features 3 distinct domains folded essentially as beta sheets, with a central domain I containing the N-terminus, a fusion domain II that is made from two polypeptide segments emanating from domain I, and a C-terminal domain III displaying an immunoglobulin superfamily fold located at the opposite side of domain I in the pre-fusion conformation. The conformational change leads to a trimerization during which the subunits adopt a hairpin conformation, bringing together the fusion loop and the trans-membrane segment, with domain III displaced by about 30-40 Å with respect to the other two domains, stabilizing the post-fusion homotrimer.

The similarities mentioned above have led to the proposal of a theoretical atomistic model of HCV E2 based on the class II fold, derived from the crystal structure of the flavivirus virus E protein homodimer [1]. This model was used to fit a low-resolution cryo-EM 3D reconstruction of HCV-like particles [27]. However, no experimental data supporting these models have been obtained so far.

Several studies have addressed the mechanism of membrane fusion initiated by the HCV glycoproteins [28-30], however the identity of the HCV fusion protein remains to be experimentally determined. Structural studies on E2 can provide important insights into its role during entry. Such studies can only come from the use of recombinant proteins, complemented by low resolution studies of authentic HCV virions. X-ray crystallography analyses on the individual proteins are however difficult, mainly because both E1 and E2 are heavily glycosylated [31]- and the presence of several glycans has been shown to be essential for folding in the ER lumen [32]. Their 3D fold is further stabilized by an important number of disulfide bridges—E1 and E2 display 8 and 18 strictly conserved cysteines, which are believed to be involved in 4 and 9 intramolecular disulfide bridges, respectively. These features concur to make production of the purified glycoproteins in sufficient quantities for structural studies a very difficult task.

DETAILED DESCRIPTION OF THE PREFERRED EMBODIMENTS

The inventors have designed Hepatitis C virus (HCV)-derived polypeptides and nucleic acid molecules encoding same which advantageously comprises a cd81-binding region. In this connection, the present invention specifically relates to the use of said polypeptides or nucleic acid molecules in compositions and methods for the prevention, the treatment and the diagnosis of HCV infections.

Definitions

The term "isolated" is meant to describe a nucleic acid construct or a polypeptide that is in an environment different from that in which the nucleic acid construct or the polypeptide naturally occurs.

The term "specifically binds to" or "having binding specificity for" refers to antibodies that bind with a relatively high affinity to one or more epitopes of the polypeptide of the invention, but which do not substantially recognize and bind molecules other than the HCV-derived polypeptides of the invention. As used herein, the term "relatively high affinity" means a binding affinity between the antibody and the polypeptide of at least $10^6 M^{-1}$, or may be of at least about $10^7 M^{-1}$ or even may be at least about $10^8 M^{-1}$ to about $10^{10} M^{-1}$. Determination of such affinity may be conducted under standard competitive binding immunoassay conditions which are common knowledge to one skilled in the art.

The term "treating" refers to a process by which the symptoms of an infection or a disease associated with a HCV strain are alleviated or completely eliminated. As used herein, the term "preventing" refers to a process by which symptoms of an infection or a disease associated with a HCV strain are obstructed or delayed.

Polypeptides and Polynucleotides of the Invention

It is therefore an object of the invention to provide Hepatitis C virus (HCV)-derived polypeptides which advantageously comprise a cd81-binding region. Such a HCV-derived polypeptide consists of an isolated polypeptide comprising or consisting of a peptide chosen from:

(a) a peptide substantially identical to an amino acid sequence comprising SEQ ID NO: 1 or 2;

(b) a peptide substantially identical to an amino acid sequence comprising SEQ ID NO: 3 or 4; or (c) a peptide substantially identical to an amino acid sequence comprising SEQ ID NO: 5, 6 or 7.

By "substantially identical" when referring to an amino acid sequence, it will be understood that the polypeptide of the present invention preferably has an amino acid sequence having at least 75% identity, or even preferably 85% identity, or even more preferably 95% identity to part or all of the sequence of SEQ ID NO: 1 to 7.

The polypeptide of the invention also comprises or consists of a peptide chosen from:

(d) a peptide comprising or consisting of a sequence chosen from SEQ ID NO: 1, 2, 3, 4, 5, 6 or 7; or (e) a peptide generating anti-HCV antibodies (e.g. neutralizing antibodies) having binding specificity for a peptide having or consisting of an amino acid sequence chosen from SEQ ID NO: 1, 2, 3, 4, 5, 6 or 7. It will be understood that the neutralizing antibodies advantageously inhibit the HCV binding to cd81. By "inhibit" is meant having the ability to interfere with the binding of a HCV strain to the B-cell cd81 receptor.

SEQ ID NO: 1 and 2 respectively represent domain I of the E2 protein of HCV H77 (genbank accession GI:130461) and UKN2b_2.8 (genbank accession AY734983) strains. SEQ ID NO: 3 and 4 respectively represent domain III of the E2 protein of HCV H77 and UKN2b_2.8 strains. SEQ ID NO: 5 and 6 respectively represent domain I+III of the E2 protein of HCV H77 strain without and with a linker. SEQ ID NO: 7 represents domain I+III of the E2 protein of HCV UKN2b_2.8 strain with a linker.

The HCV-derived polypeptide of the present invention also relates to a soluble fragment of HCV E2 protein, wherein the fragment consists of the contiguous amino acids from the N-terminus of the E2 protein to the last amino acid before the transmembrane domain of the E2 protein, and is produced, in particular recombinantly produced, in an insect cell, in particular a Drosophila cell, more particularly in a Schneider 2 (S2) cell.

In particular, the soluble fragment of HCV E2 protein corresponds to amino acids 384 to 715 of the polyprotein of HCV H77 strain. The polyprotein of HCV H77 strain is notably represented by genbank accession number GI:130461 and amino acids 348 to 715 of the polyprotein of HCV H77 strain are represented by SEQ ID NO: 15. It is well within the common skills of one of skill in the art to identify sequences from other HCV strains corresponding to, homologous to, or aligning with amino acids 384 to 715 of the polyprotein of HCV H77 strain. By way of example, FIG. 4 represents a sequence alignment of soluble fragments of HCV E2 protein according to the invention from HCV H77, JFH-1 (notably defined by genbank accession GI:116078059) and UKN2B-2.8 (notably defined by genbank accession AY734983) strains, which are respectively represented by SEQ ID NO: 15, 16 and 17. Thus, the present invention also relates to a soluble fragment of HCV E2 protein, wherein the fragment consists of SEQ ID NO: 15, 16, or 17, and is produced in an insect cell, in particular a Drosophila cell, more particularly in a Schneider 2 (S2) cell.

As will be clear to one of skill in the art, as intended herein a "soluble" polypeptide is preferably such that it does not precipitate in an aqueous medium, such as cytoplasm, a cell culture medium, or a standard protein conservation medium, in particular for a period of at least 1 month at 4° C.

It is also an object of the invention to provide an isolated nucleic acid molecule which encodes for the polypeptides of the invention. More particularly, the nucleic acid molecule of the invention comprises a polynucleotide chosen from:

(a) a polynucleotide encoding a peptide substantially identical to an amino acid sequence comprising SEQ ID NO: 1 or 2 or fragments or analogs thereof;

(b) a polynucleotide encoding a peptide substantially identical to an amino acid sequence comprising SEQ ID NO: 3 or 4 or fragments or analogs thereof; or (c) a polynucleotide encoding a peptide substantially identical to an amino acid sequence comprising SEQ ID NO: 5, 6 or 7 or fragments or analogs thereof.

The nucleic acid molecule of the invention also comprises a polynucleotide chosen from:

(d) a polynucleotide encoding a peptide comprising a sequence chosen from SEQ ID NO: 1, 2, 3, 4, 5, 6 or 7 or fragments or analogs thereof; or (e) a polynucleotide encoding a peptide generating anti-HCV antibodies having binding specificity for a peptide having an amino acid sequence chosen from SEQ ID NO: 1, 2, 3, 4, 5, 6 or 7 or fragments or analogs thereof.

More particularly, the nucleic acid molecule of the invention may comprise a nucleotide sequence substantially identical to SEQ ID NOS 8, 9, 10, 11, 12, 13 or 14.

By "substantially identical" when referring to a nucleic acid sequence, it will be understood that the polynucleotide of the invention preferably has a nucleic acid sequence which is at least 65% identical, more particularly 80% identical and even more particularly 95% identical to part or all of the sequence shown in SEQ ID NOS 8 to 14 or functional fragments thereof.

A "functional fragment", as is generally understood and used herein, refers to a nucleic acid sequence that encodes for a functional biological activity that is substantially similar to the biological activity of the whole nucleic acid sequence. In other words, and within the context of the present invention, it preferably refers to a nucleic acid or fragment(s) thereof that substantially retains the capacity of encoding a polypeptide/protein which elicits antibodies, and more preferably neutralizing antibodies, to a HCV strain challenge when administered to an animal.

In another object, the invention is further directed to a vector (e.g., a cloning or expression vector) comprising a polynucleotide of the invention as defined above.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

A number of vectors suitable for stable transfection of cells and bacteria are available to the public (e.g., plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present invention encompasses any type of vector comprising any of the polynucleotide molecule of the invention.

Another object of the present invention is to provide a host cell transfected with a vector as defined above. It is understood that any suitable cell to one skilled in the art may be used in accordance with the present invention. In a related aspect, there is provided a method for producing a polypeptide as defined above, comprising culturing a host cell of the invention under conditions suitable for expression of said polypeptide and harvesting said expressed polypeptide. It will be understood that the conditions for expression may be those described in the Example section.

Compositions and Methods of Use of the Invention

The HCV-derived polypeptides, in particular the soluble fragment of HCV E2 protein, and nucleic acid molecules encoding same of the invention may be used in many ways in the treatment and/or prevention of infection caused by HCV.

For instance, and according to an aspect of the invention, the HCV-derived polypeptides, in particular the soluble fragment of HCV E2 protein, of the invention may be used as immunogens for the production of specific antibodies (e.g. neutralizing antibodies) for the treatment and/or prevention of a HCV infection.

The present invention thus also relates to the HCV-derived polypeptides, in particular the soluble fragment of HCV E2 protein, of the invention for use for the prevention and/or treatment of a HCV infection.

In a related aspect, there is provided a method for producing antibodies neutralizing entry of HCV into a cell. Such a method comprises the steps of:

(a) administering to a suitable host a polypeptide or a soluble fragment of HCV E2 protein of the invention, a nucleic acid molecule of the invention, or a composition as defined above to produce HCV neutralizing antibodies and (b) harvesting said HCV neutralizing antibodies.

The present invention also relates to a method for producing anti-HCV antibodies or B-lymphocytes, comprising a step of harvesting said anti-HCV antibodies or B-lymphocytes in a biological sample, such as a blood, serum or plasma sample, from a non-human animal which has been administered a HCV-derived polypeptide, in particular a soluble fragment of HCV E2 protein, according to the invention. In a further step, anti-HCV monoclonal antibodies may be generated from the B-lymphocytes.

Suitable antibodies may be determined using appropriate screening methods, for example by measuring the ability of a particular antibody to neutralize the HCV infection in a cellular test model. Examples of such cellular test model are well known to one skilled in the art and will not be discussed further.

The present invention also relates to the in vitro use of a HCV-derived polypeptide, in particular a soluble fragment of HCV E2 protein, according to the invention for generating specific ligands of HCV. The ligands may be of any nature. However, it is preferred that the ligands are scFv fragments, or peptide or nucleotide aptamers.

According to another aspect, the nucleic acid molecules encoding polypeptides of the invention or derivatives thereof may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. For instance, the vector may be injected intramuscularly. The use of a nucleic acid molecules of the invention in genetic immunization will preferably employ a suitable delivery method or system such as direct injection of plasmid DNA into muscles [Wolf et al. H M G (1992) 1: 363, Turnes et al., Vaccine (1999), 17: 2089, Le et al., Vaccine (2000) 18: 1893, Alves et al., Vaccine (2001) 19: 788], injection of plasmid DNA with or without adjuvants [Ulmer et al., Vaccine (1999) 18: 18, MacLaughlin et al., J. Control Release (1998) 56: 259, Hartikka et al., Gene Ther. (2000) 7: 1171-82, Benvenisty and Reshef, PNAS USA (1986) 83: 9551, Singh et al., PNAS USA (2000) 97: 811], targeting cells by delivery of DNA complexed with specific carriers [Wa et al. J Biol Chem (1989) 264: 16985, Chaplin et al., Infect. Immun. (1999) 67:6434], injection of plasmid complexed or encapsulated in various forms of liposomes [Ishii et al., AIDS Research and Human Retroviruses (1997) 13: 142, Perrie et al., Vaccine (2001) 19:3301], administration of DNA with different methods of bombardment [Tang et al., Nature (1992) 356: 152, Eisenbraun et al., DNA Cell Biol (1993) 12: 791, Chen et al., Vaccine (2001) 19:2908], and administration of DNA with lived vectors [Tubulekas et al., Gene (1997) 190: 191, Pushko et al., Virology (1997) 239: 389, Spreng et al. FEMS (2000) 27: 299, Dietrich et al., Vaccine (2001) 19: 2506].

In this connection, another aspect of the present invention relates to a composition, in particular a pharmaceutical composition, more particularly a vaccine composition, for preventing or treating such HCV infections. The composition of the present invention advantageously comprises an acceptable carrier and a polypeptide(s) of the invention or a soluble fragment of HCV E2 protein of the invention. Alternatively, the composition of the invention can comprise a nucleic acid molecule and/or an expression vector of the invention.

In a preferred embodiment, the composition of the invention further comprises an adjuvant. As used herein, the term "adjuvant" means a substance added to the composition of the invention to increase the composition's immunogenicity. The mechanism of how an adjuvant operates is not entirely known. Some adjuvants are believed to enhance the immune response (humoral and/or cellular response) by slowly releasing the antigen, while other adjuvants are strongly immunogenic in their own right and are believed to function synergistically. Known adjuvants include, but are not limited to, oil and water emulsions (for example, complete Freund's adjuvant and incomplete Freund's adjuvant), Corytzebactei-ium parvuin, Quil A, cytokines such as IL 12, Emulsigen-Plus®, *Bacillus* Calmette Guerin, aluminum hydroxide, glucan, dextran sulfate, iron oxide, sodium alginate, Bacto Adjuvant, certain synthetic polymers such as poly amino acids and co-polymers of amino acids, saponin, paraffin oil, and muramyl dipeptide. Adjuvants also encompass genetic adjuvants such as immunomodulatory molecules encoded in a co-inoculated DNA, or as CpG oligonucleotides. The coinoculated DNA can be in the same plasmid construct as the plasmid immunogen or in a separate DNA vector.

Yet, a further aspect of the present invention is to provide a method for treating and/or preventing a Hepatitis C virus (HCV) infection in a host. The method of the invention comprises the step of administering to the host a polypeptide, a soluble fragment of HCV E2 protein and/or a nucleic acid molecule and/or a composition as defined above. The host may be an animal such as a human.

Further agents can be added to the composition of the invention. For instance, the composition of the invention may also comprise agents such as drugs, immunostimulants (such as α-interferon, β-interferon, γ-interferon, granulocyte macrophage colony stimulator factor (GM-CSF), macrophage colony stimulator factor (M-CSF), and interleukin 2 (IL2)), antioxidants, surfactants, flavoring agents, volatile oils, buffering agents, dispersants, propellants, and preservatives. For preparing such compositions, methods well known in the art may be used.

The amount of the components or the elements of the composition of the invention is preferably a therapeutically effective amount. A therapeutically effective amount of the contemplated component is the amount necessary to allow the same to perform their immunological role without causing overly negative effects in the host to which the composition is administered. The exact amount of the components to be used and the composition to be administered will vary according to factors such as the type of condition being treated, the type and age of the host to be treated, the mode of administration, as well as the other ingredients in the composition.

The composition of the invention may be given to the host through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection, by infusion or per os. Suitable dosages will vary, depending upon factors such as the amount of each of the components in the composition, the desired effect (short or long term), the route of administration, the age and the weight of the host to be treated. Any other methods well known in the art may be used for administering the composition of the invention.

Methods of Detection or Diagnosis and Kits

The HCV polypeptides and nucleic acid molecules encoding same of the invention may also be used in different ways in the detection and diagnosis of HCV infection.

In this connection and in a further aspect, the present invention provides a method for diagnostic of HCV infection in a host susceptible to HCV infection comprising the steps of:

(a) incubating an antibody or fragment thereof that specifically binds to a polypeptide or soluble fragment of HCV E2 protein as defined above with a biological sample obtained from a host to form a mixture; and (b) detecting specifically bound antibody or bound fragment in the mixture which indicates the presence of HCV.

As used herein, the term "sample" refers to a variety of sample types obtained from the host and can be used in a diagnostic or detection assay. The definition encompasses blood and other liquid samples of biological origin, solid tissue samples such as a biopsy specimen or tissue culture or cells derived therefrom.

Yet, in another embodiment, the present invention provides a method for detection of antibody specific to HCV antigen in a biological sample comprising the steps of:

(a) incubating a polypeptide of the invention or fragments thereof, or a soluble fragment of HCV E2 protein, with a biological sample obtained from a host to form a mixture; and (b) detecting specifically bound polypeptide or bound fragment in the mixture which indicates the presence of antibody specific to HCV.

One skilled in the art will recognize that this diagnostic test may take several forms, including an immunological test such as an enzyme-linked immunosorbent assay (ELISA) or a radioimmunoassay, essentially to determine whether antibodies specific for the HCV protein (such as E2) are present in an organism.

The present invention further provides kits for use within any of the above diagnostic methods. Such kits typically comprise two or more components necessary for performing a diagnostic assay. Components may be compounds, reagents, containers and/or equipment. For example, one container within a kit may contain an antibody or fragment thereof that specifically binds to a HCV polypeptide of the invention. One or more additional containers may enclose elements, such as reagents or buffers, to be used in the assay.

In this connection, the present invention also provides a kit comprising a polypeptide and/or a soluble fragment of HCV E2 protein and/or a nucleic acid molecule of the invention for detection or diagnosis of HCV infection. Such a kit may further comprise a reagent to detect polypeptide-antibody immune complex, a biological reference sample lacking antibodies that immunologically bind with the HCV peptide. The kit may also comprise a comparison sample comprising antibodies which can specifically bind to the HCV peptide. It will be understood that the HCV polypeptide, reagent, biological reference sample, and comparison sample are advantageously present in an amount sufficient to perform said detection.

Figures 2A, 2B:
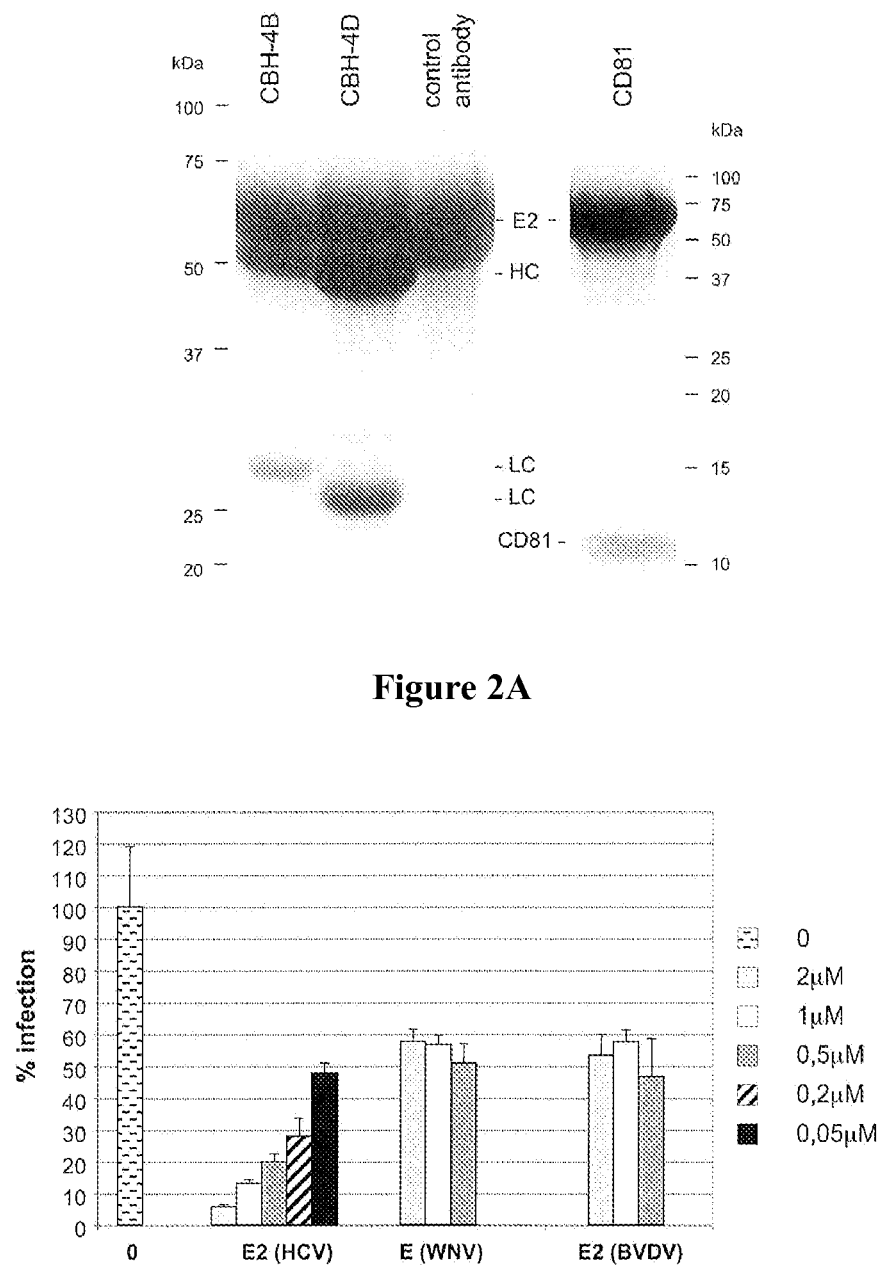

FIGS. 2A and 2B: Characterization of recombinant soluble HCV E2 expressed in *Drosophila* S2 cells FIG. 2A: Soluble E2 was able to pull down a soluble large extracellular loop of CD81 as well as the conformation dependent antibodies CBH-4B and CBH-4D (kindly provided by S. Foung, Stanford), but not a control antibody. Eluted complexes were concentrated and separated by SDS-PAGE under reducing conditions followed by Coomassie staining. Bands representing the soluble E2, CD81-LEL as well as the heavy chain (HC) and light chain (LC) of the two antibodies were observed.

FIG. 2B: Equal numbers of HuH-7 cells were preincubated 1 h at 23° C. with increasing concentrations of recombinant soluble HCV E2, West Nile virus (WNV) E protein or BVDV E2, respectively, and subsequently infected with ~$10^3$ ffu JFH-1 in the corresponding protein concentration for 4 h at 37° C. 72 h p.i. cells were fixed and the number of infectious foci was determined after immunofluorescence analysis detecting intracellular HCV core antigen. While WNV E protein and BVDV E2 displayed an unspecific effect on susceptibility to infection with JFH-1 independent of the used concentration, for HCV E2 clearly a dose dependent inhibition could be observed. The columns represent mean values of duplicates in a representative experiment, bars indicate mean deviation.

FIGS. 3A and 3B: CD spectra of envelope glycoproteins

FIG. 3A: Highly purified soluble HCV E2 (σ), Chikungunya E1 (●) and West Nile virus E protein (♦) were used for circular dichroism of envelope glycoproteins at room temperature. Secondary structure contents were estimated from the far-UV CD spectra using the CDSSTR routine of the DICHROWEB server run on the SP175 database. Although the CD spectra of the three different proteins are very different, the estimated secondary structure content is highly similar.

FIG. 3B: FTIR spectra of sE2 (dashed black line) and DV2 sE (solid black line) and the difference spectrum of the two after normalization (dashed grey line) in the amide I band region.

Figure 4:
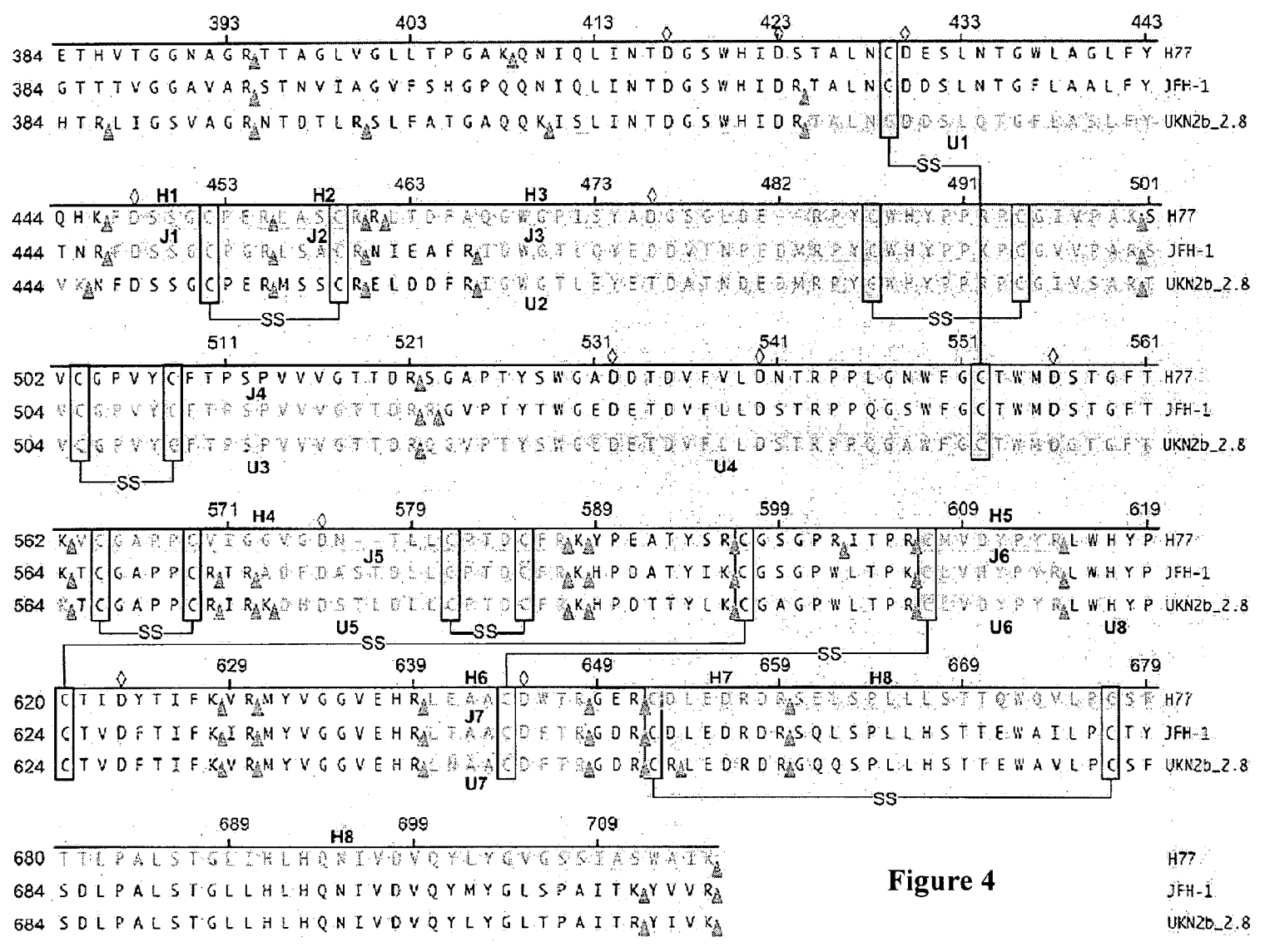

FIG. 4: Analysis of HCV E2 sequences from strains H77, JFH-1 and UKN2b_2.8 HCV E2 ectodomain amino acid sequences, ending at aa715 (numbering according to strain H77) from strains H77 (genbank accession GI:130461) (SEQ ID NO: 15), JFH-1 (genbank accession GI:116078059) (SEQ ID NO: 16) and UKN2b_2.8 (genbank accession AY734983) (SEQ ID NO: 17) were aligned. Given that deglycosylation by PNGase F results in change of the amino acid from asparagine to aspartic acid, the predicted N-glycosylation sites are displayed as aspartic acid residues.

Predicted trypsin cleavage sites (σ) and N-glycosylation sites (◊) are indicated, cysteines are boxed and the respective disulfide bridges are shown (-SS-). Peptides identified after tryptic cleavage are shaded, named according to the respective isolate and numbered sequentially following the amino acid sequence of E2.

Figure 5A:
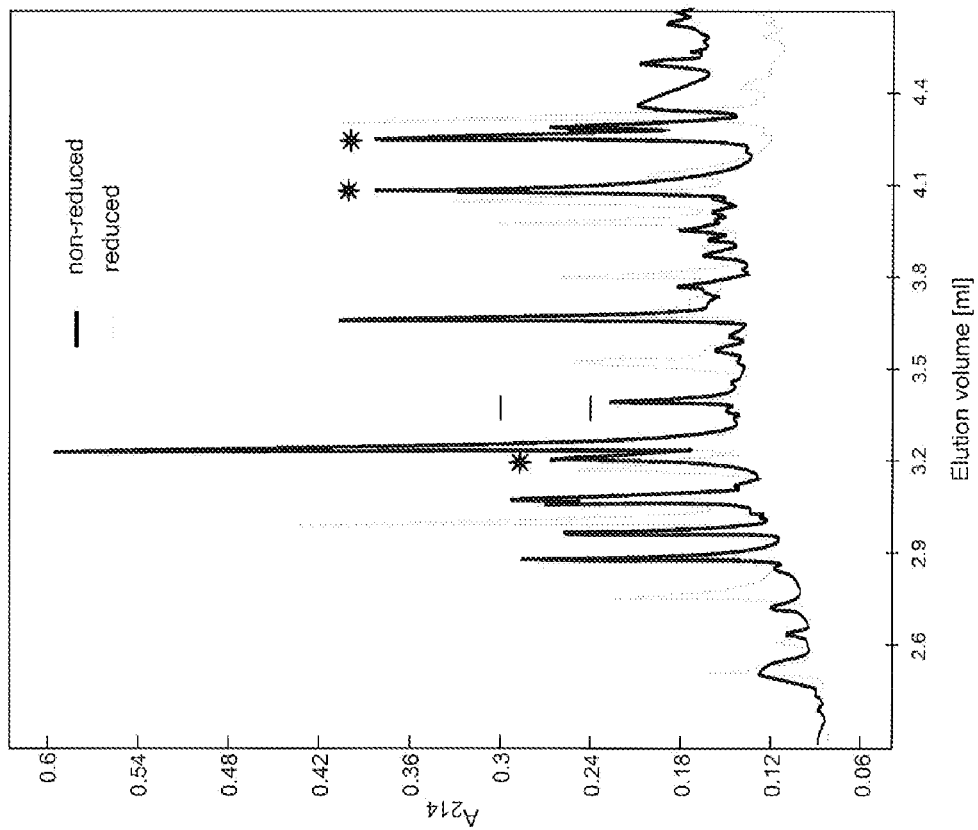
Figure 5B:
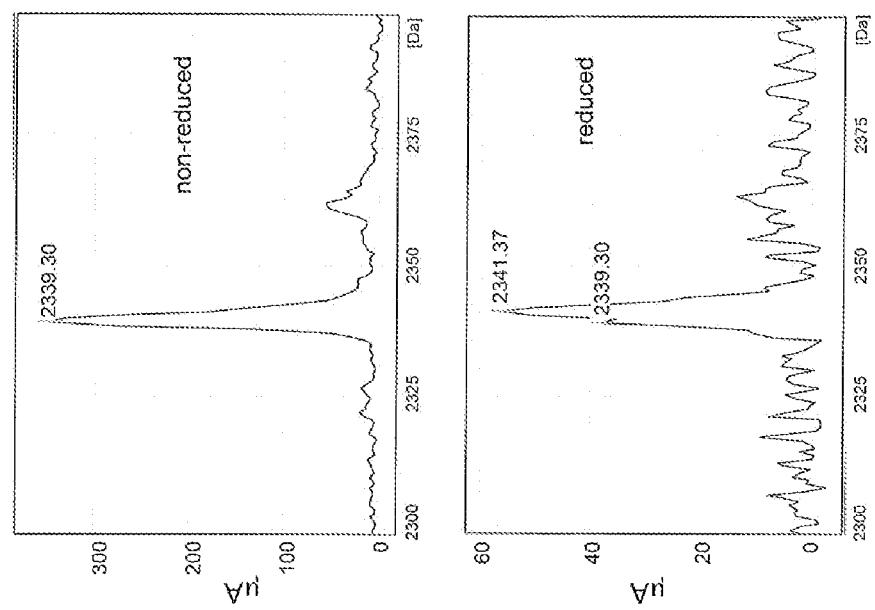

FIGS. 5A and 5B: Disulfide mapping strategy

FIG. 5A: Example of a partial profiles of the HPLC's of a HCV E2 tryptic digestion under non-reduced (black) and reduced (light grey) conditions are superposed to illustrate the differences in HPLC profiles. Peaks labelled with asterisks disappeared upon reduction and were selected for further proteomic analysis.

FIG. 5B: Exemplary result of mass spectrometry of a HPLC peak that disappeared upon reduction. Shown is the result for Peak 16-3 of JFH-1 E2 identified as peptide J4 by N-terminal sequencing containing two cysteines enclosing a proline. Upon reduction a shift in molecular mass of 2 Da was observed, likely due to addition of two hydrogen atoms upon reduction of the two cysteines.

Figure 6:
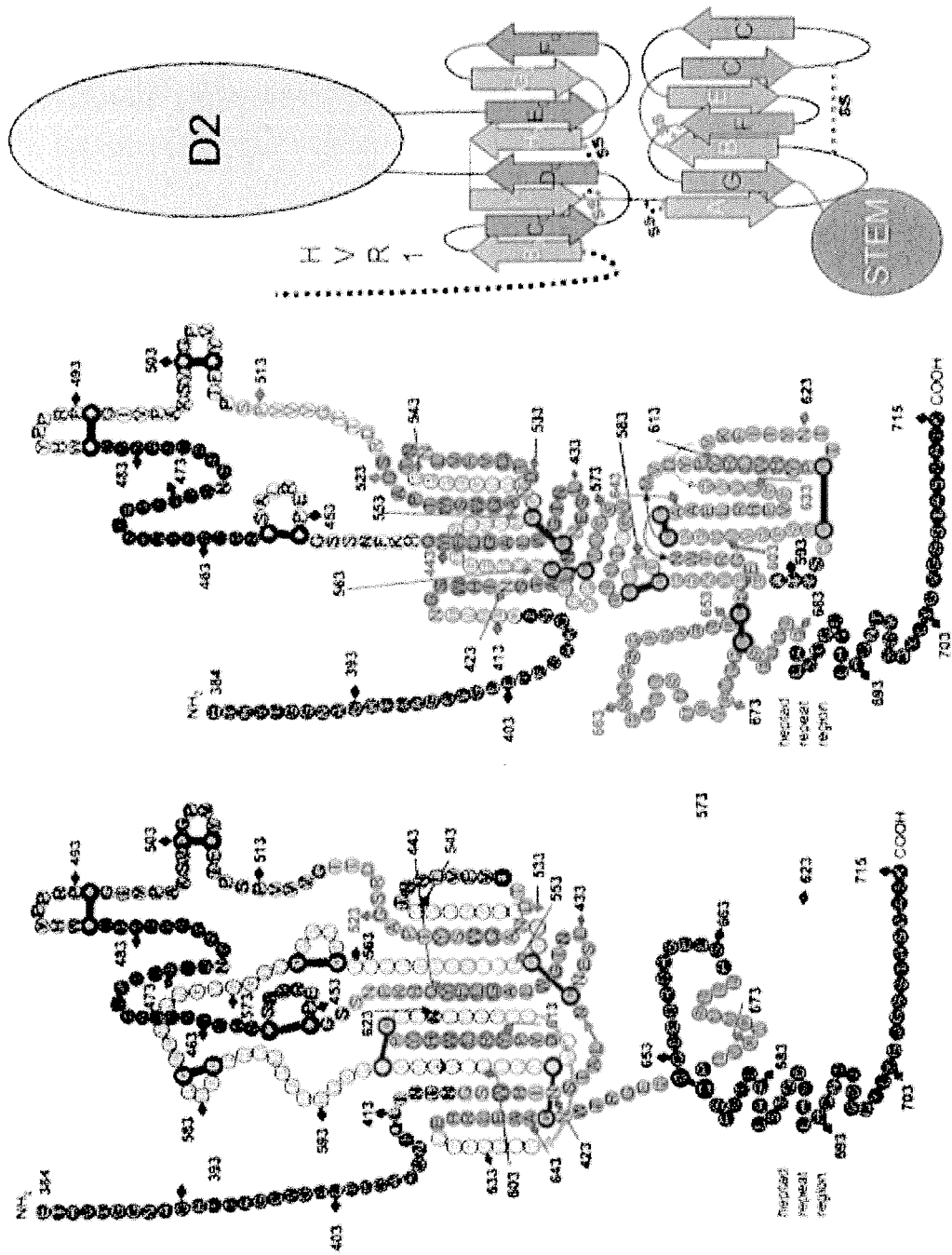

FIG. 6: Schematic model of the HCV E2 ectodomain Based on the experimentally disulfide connectivity pattern the ectodomain of HCV E2 was modelled using the class II viral fusion protein fold as template. N- and C-Terminus are indicated. The same colour code for the three distinct domains was used as in similar figures showing TBEV E and SFV E1 [51, 60] and a schematic drawing is appended to illustrate the domain organization in HCV E2. While in TBEV E as well as SFV E1 two long insertions between strands in the central domain form the dimerization domain II, in HCV E2 only one insertion forms the tip domain II. In contrast, domain III, which has previously been predicted not to be present, has got a similar size as in TBEV E or SFV E1, however the extended stem region seems to contain one of the nine disulfide bridges. Residues that have been previously reported to be involved into CD81 binding are encircled, the disulfide bridges are indicated by black bars.

Figure 7:
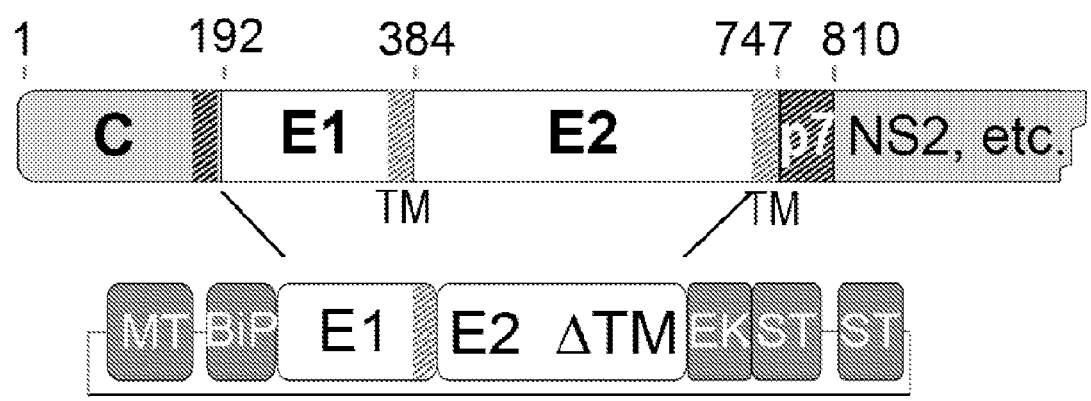

FIG. 7: Schematic diagram of the HCV genome region coding for the structural proteins and the construct used to make stable S2 cell transfectant expressing $sE2_{715}$.

EXAMPLES

Disulfide Bonds of the Hepatitis C Virus Glycoprotein E2

Implications for its 3D Fold

Envelope glycoproteins are key players in the replication cycle of enveloped viruses. In addition to carrying the main antigenic determinants, these proteins are responsible for receptor recognition and triggering fusion of the viral and cellular membrane during viral entry. The inventors report here a biochemical and preliminary structural characterization of recombinant glycoprotein E2 from the hepatitis C virus, a major human pathogen. An expression system for the ectodomain of HCV E2 (sE2) was established using *Drosophila* S2 cells, which allows the production of large quantities of correctly folded monomeric protein, as assayed by a number of conformational and functional tests. sE2 was used to analyze the secondary structure composition of the folded protein and to determine the connectivity of the disulfides. Together, these data have strong implications for the overall 3D fold of the protein, and the possible tertiary structure based in the class II fold is discussed.

Materials and Methods
Cells, Viruses and Media

*Drosophila* Schneider 2 (S2) cells were purchased from Invitrogen and cultured at 28° C. in Schneiders *Drosophila* medium (Invitrogen, Carlsbad, USA). Stable cell lines were transferred to serum-free Insect Xpress media (Lonza, Basel, Switzerland), which was also used for protein production. Human hepatoma cells (Huh 7.5) [33] were cultured in Dulbecco's Modified Eagle Medium supplemented with 10% fetal bovine serum (FBS), 100 U/ml penicillin, 100 μg/ml streptomycin, and a 100 μM mixture of non-essential amino acids (DMEM-10%, all reagents from Invitrogen, Cergy-Pontoise, France) and maintained at 37° C. in a 5% $CO_2$ atmosphere.

HCV stocks (HCVcc) were produced after electroporation of cB76.1/Huh7 cells [34] with RNA transcripts synthesized in vitro from pJFH1 [35]. Cell supernatants were harvested at 7 days post-transfection and virus titers (in focus forming units (FFU)/mL) were determined by indirect immunofluorescence on Huh7.5 cells, as described below.

Plasmids

For improved purification efficiency the region encoding the V5-His Tag in the plasmid pMT/BiP/V5-His was replaced by a region encoding an Enterokinase cleavage site and a double Strep Tag separated by a linker region $(GGS)_4$ (SEQ ID NO: 18), resulting in the following amino acid sequence downstream of the ApaI and BstBI sites . . . DDDDKAGW-SHPQFEKGGGSGGGSGGGSWSHPQFEK-COOH (SEQ ID NO: 19). All synthetic HCV glycoprotein genes were purchased from GeneCust (Dudelange, Luxemburg) and amplified by PCR using strain specific 5'-oligonucleotides containing BgI II, which allows insertion immediately downstream of the BiP secretion signal, and strain specific 3'-oligonucleotides containing Apa I.

A full list of oligonucleotides used in this study is available upon request.

Generation of Inducible *Drosophila* S2 Cell Lines Producing sE2

2 μg of the respective plasmid was transfected into *Drosophila* S2 cells using Effectene (Qiagen, Hilden, Germany) according to the manufacturers recommendations. A plasmid encoding either Blasticidin S deaminase or puromycin acetyltransferase, respectively, was cotransfected as dominant selectable marker. Stable sE2 expressing cell lines were selected by addition of 6 μg/ml Puromycin or 25 μg/ml Blasticidin S (Invivogen, San Diego, USA) to the culture medium 72 h after transfection. Adaptation of the cell lines to serum free Insect Xpress media was performed stepwise as recommended by Invitrogen. Expression systems for West-Nile virus E protein, E2 of bovine viral diarrhea virus as well as for E1 of Chikungunya virus were designed in a similar way.

Production and Purification of Envelope Glycoprotein

For large scale production of sE2 the cells were cultured in spinner flasks or in Wave Bioreactors (2/10, Wave Biotech, Somerset, USA) and induced with 4 μM $CdCl_2$ at a density of approximately $7\times10^6$ cells per ml. After 8 days at 28° C. cells were pelleted and sE2 in the supernatant was purified by affinity chromatography using a StrepTactin Superflow column (IBA, Goettingen, Germany) followed by gel filtration chromatography using a Superdex200 column (GE Healthcare, Uppsala, Sweden). Pure protein was quantified using adsorption at $UV_{280nm}$ and concentrated to approximately 1 mg/ml.

Pull-Down Assay of Antibodies and CD81 Using sE2

25 μg of sE2 was bound to a StrepTactin Superflow mini column and washed with 10 column volumes of washing buffer. Subsequently, 10 μg of CD81 large extracellular loop (produced as described before [36]) or 50 μg conformation dependent antibodies CBH-4B, CBH-4D against HCV E2 (kindly provided by S. Foung, Stanford, USA) or a control antibody were added followed by washing with 10 column volumes. Complexes were eluted in 4.5 column volumes elution buffer and concentrated 20-fold by ultrafiltration. This concentrate was analysed by SDS-PAGE followed by Coomassie staining.

Inhibition of HCVcc Infection by sE2

Huh7.5 cells plated on glass coverslips in 24-well plates ($4.5\times10^4$ cells per well) were incubated for 1 h at RT in the absence or presence of increasing concentrations (0.05-2 μM) of HCV sE2, or BVDV sE2 or West Nile virus sE used as controls. Cells were subsequently washed and infected with $7\times10^3$ FFU of HCVcc in the presence of identical concentrations of respective viral glycoproteins. After a 5 h adsorption period at 37° C., the viral inoculum was removed and replaced with fresh medium. At 3 days post-infection, cells were fixed with 4% paraformaldehyde, permeabilized in 0.2% Triton X-100 in PBS, and subsequently processed for core detection by indirect immunofluorescence using 0.5 μg/mL of anti-core monoclonal antibody 1851 (Abcys, Paris, France) and Alexafluor 555-conjugated anti-mouse IgG (Invitrogen) at a 1:500 dilution. Coverslips were mounted on slides using ProLong Gold Antifade Reagent with DAPI (Invitrogen) allowing counterstaining of cell nuclei. Virus titers were determined by counting labeled foci following acquisition of mosaic images spanning the entire surface of each coverslip using an Axioplan2i microscope (Zeiss) with a Wide Field ApoTome (Zeiss) and the Axiovision software (Zeiss).

Far-UV Circular Dichroism of Envelope Glycoproteins

HCV UKN2b_2.8 E2 or either of the control proteins in a concentration of 0.7 mg/ml in 20 mM phosphate pH 7.5, 150 mM NaF were used for circular dichroism of envelope glycoproteins. CD spectra were obtained with an AVIV CD spectrophotometer model 215 using a 0.02 cm path length cell at room temperature. Five successive scans were averaged and the background spectrum of the sample buffer, acquired under identical conditions, was subtracted. The resulting corrected CD intensities were then converted to Δε per residue. Secondary structure contents were estimated from the far-UV CD spectra using the CDSSTR routine of the DICHROWEB server [37, 38] run on the SP175 reference dataset [39]. Quality of fit was judged from normalised root mean square deviation with values <0.1 (HCV E2 0.04±0.03, for CHIK V sE1 0.060±0.02, and for WNV sE 0.05±0.00) considered as a very good fit for all three proteins.

Fourier Transform Infrared Spectroscopy of Envelope Glycoproteins

HCV E2 and E protein of Yellow Fever virus in a concentration of 5-10 mg/ml in 10 mM Tris pH 8.0, 150 mM NaCl were used for FTIR analysis. Attenuated total reflectance FTIR spectra were measured with a Bruker vector 22 spectrophotometer equipped with a 45° diamond ATR attachment (National Instruments, U.K.). The spectra shown represent the average of 100 scans after removal of the buffer signal.

Deglycosylation and Proteolytic Digestion of sE2

200 μg of sE2 were boiled 10 minutes at 95° C. in 2.5% SDS and the denatured protein was incubated with His-tagged PNGase F in excess at 37° C. overnight. Subsequently, PNGase F was removed by ion metal affinity purification, the deglycosylated protein was concentrated to a concentration of approximately 1.5 mg/ml and analysed by SDS-PAGE followed by staining with Amido Black. Bands containing approximately 15 μg sE2 were cut out of the gel and subsequently digested at 37° C. in 0.01% Tween20, 50 mM TrisHCl with 0.5 μg Trypsin. In order to stabilize existing disulfide bonds the pH of the reaction was set to the lowest possible value (pH 7.0 for experiment 1, pH 7.6 for experiment 2 and pH 8.6 for experiment 3), which resulted in efficient digestion. After 8 h 0.25 μg Trypsin were added and the digestion was continued for further 16 h. The peptides were eluted from the gel using 200 μl water and two times 100 μl 60% Acetonitril.

For a control experiment the tryptic digest was performed as described above, but in presence of 5% DMSO, acting as oxidizing agent. For digestion in Nitrocellulose membrane the deglycosylated protein was analysed by SDS-PAGE followed by transfer onto a Nitrocellulose membrane and staining with Poinceau-Red. Bands containing approximately 15 µg sE2 were cut out of the membrane and saturated with 1 ml of 0.2% PVP K30 for 15 minutes followed by four washes with water and two washes with 50 mM TrisHCl pH 7.6. Subsequently the protein was digested with 1 µg Trypsin for 3 h at 37° C. in the absence or presence of 5 mM NEM. The peptides were eluted from the membrane using 200 µl water.

HPLC of Resulting Peptides and Subsequent Proteomic Analysis

Half of the tryptic digest was separated by reverse-phase HPLC using DEAE-C18 columns (1 mm diameter) and a gradient of 2 to 70% Acetonitrile in TFA 0.1%. The second half of the tryptic digest was reduced by addition of TCEP to a final concentration of 2.5 mM (for the control experiment including NEM 10 mM TCEP were used) for 30 minutes at RT and subsequently subjected to reverse-phase HPLC under identical conditions (FIG. 5a). Peaks corresponding to HPLC-separated peptides under non-reducing conditions were serially numbered and peaks that disappeared upon reduction were selected for further analysis by N-terminal sequencing and Surface-Enhanced Laser Desorption/Ionisation-Time-Of-Flight Mass Spectrometry (SELDI-TOF MS) using H4-protein chips (Ciphergen, Goettingen, Germany).

N-Terminal Sequencing and SELDI-TOF Analysis

N-terminal sequencing was performed using a ABI 494 Protein Sequencer (Applied BioSystems, Foster City, USA). SELDI-TOF analysis was performed on a Protein ChipReader System 4000 using a H4 (reversed phase, Ciphergen Biosystems, Fremont, Calif., USA) surface and a SPA matrix, which was prepared according to the manufacterer's instructions. Peak identification was carried out using ProteinChip Software 3.1 (Ciphergen). Molecular weight prediction of disulfide-connected peptides was performed using MS-BRIDGE [40], while molecular weight of reduced peptides was predicted using PeptideMass [41].

Results

Expression and Characterization of Soluble HCV E2

The inventors adapted the *Drosophila* Expression System (DES, Invitrogen) for expression of the full ectodomain of HCV E2 glycoproteins from a number of strains for large-scale production and purification from the cell culture medium. The Invitrogen pMT/BiP vector was modified to encode for an engineered sE2 protein such that it can be efficiently purified upon induction of the metallothionin promoter with divalent cations ($Cu^{2+}$ or $Cd^{2+}$). The original vector encodes the *Drosophila* BiP signal sequence (SS) at the N-terminus of the construct for efficient translocation into the ER of the S2 cells, in frame with the gene of the secreted protein of interest (replacing the endogenous SS). At the C-terminal end, the pMT/BiP vector includes a segment coding for the V5 epitope followed by a 6-Histidine tag allowing NTA affinity purification. In order to avoid an interaction of the divalent metal ions used for induction with the histidine tag in the secreted protein, this region was replaced in our construct by a segment coding for a specific proteolytic cleavage site, followed by a double strep-tag peptide (IBA, www.iba-go.com). This is a tandem strep-tag with a linker region $(GlyGlySer)_4$ (SEQ ID NO: 18) in between. The proteolytic cleavage site was added to allow the specific removal of the tag for structural studies. Because of the high susceptibility of class II viral envelope proteins to reducing agents, the inventors avoided using cysteine-proteases such as the TEV or the picornavirus 3C (or "Prescission" protease)—which require a reducing agent for their activity. The inventors included instead an enterokinase (EK) cleavage site, which is a serine-protease that is relatively specific for the sequence $(Asp)_4$Lys↓X, cleaving at the site indicated by the arrow with a cleavage efficiency between 60 and 80% for X being any amino acid [42]. The engineered production vector was termed pMT/BiP/EK2ST.

Numerous studies on HCV E2 have been reported in the literature using soluble E2 truncated at $aa_{661}$ (protein $sE2_{661}$; this numbering refers to the precursor polyprotein of HCV strain H77c, genotype 1a, and is used throughout this manuscript). This protein is efficiently secreted into the supernatant and was shown to be recognized by conformational antibodies and to bind to the candidate cellular receptors CD81 and SR-BI [43, 44]. $sE2_{661}$ lacks the C-terminal cysteine (Cys677), leaving an unpaired cysteine residue (out of the 18 strictly conserved cysteines present in the protein), resulting in the formation of non-specific disulfide linked multimers. To avoid these difficulties, the inventors cloned the intact E2 ectodomain, truncated just upstream of the putative TM segment.

The inventors inserted the coding sequence spanning residues 191 to 715 (or equivalent after multiple alignments)—beginning at the authentic N-terminus of E1 generated by signalase—from 9 HCV strains into the pMT/BiP/EK2ST vector (FIG. 7). The rationale for including the E1 coding sequence was to allow for a putative chaperoning role during folding of E2 [45]. The strains used belong to all 6 genotypes as well as 4 subtypes, selected upon previously published results demonstrating that the individual sequences are functional for entry of retroviral particles pseudotyped with HCV glycoproteins (HCVpp) [46]. The inventors used synthetic DNA optimized for the *Drosophila* codon usage to make the constructs, which were used to transfect S2 cells to obtain inducible cell lines secreting $sE2_{715}$. Induction was found to be most efficient by using 4 μM $CdCl_2$ at a cell density of $7\times10^6$ cells per nil. The secreted proteins were purified as described in materials and methods. The inventors found considerably different expression levels depending on the strain, as well as different tendencies to form misfolded disulfide linked aggregates (FIG. 1). However, the monomeric soluble protein of all strains used, separated from the aggregates by size exclusion chromatography, remained monomeric even after several months at 4° C. without displaying any further tendency to aggregate (data not shown). The inventors identified strain UKN2b_2.8 (genbank accession AY734983)—from genotype 2b as producing the highest yield of recombinant monomeric protein. This protein was used for most of the experiments, except when specifically indicated.

The inventors characterized the purified $sE2_{715}$ by investigating the binding of two anti HCV E2 monoclonal antibodies recognizing conformational epitopes (CBH-4B and CBH-4D, [47] kindly provided by S. Foung), as well as recombinant CD81-LEL produced as described previously [36].

For this purpose $sE2_{715}$ was bound to a Strep-Tactin column and an equimolar ratio of either CD81 or monoclonal antibody was loaded. After washing the complex was eluted, concentrated approximately 20-fold and analyzed in SDS-Page followed by Coomassie staining. sE2 was able to pull down CD81 as well as both conformation-dependent antibodies, but not a control antibody (FIG. 2A).

Inhibition of HCVcc by HCV E2 Produced in *Drosophila* Cells

As an additional control of the functionality of the recombinant $sE2_{715}$ protein, the inventors tested its capacity to inhibit HCVcc infection of Huh7.5 cells. It was previously reported that soluble $E2_{715}$ produced in mammalian cells does not inhibit HCVcc entry, even at high concentrations (≤1

μM) [48]. Inhibition of HCVcc infection of Huh7.5 cells by our *Drosophila*-produced sE2$_{715}$ was done as described in materials and methods, using as a control its pestivirus and flavivirus counterpart, BVDV sE2 and West Nile Virus sE protein, respectively. The latter two proteins were produced in the inventors' laboratory in the same way for other purposes. Irrespective of the protein concentration used, both control proteins reduced the number of HCVcc-infected foci to approximately 50-60%, as compared to foci obtained upon infection in the absence of exogenous viral glycoprotein (100%, FIG. 2B). This indicates a certain level of non-specific inhibition of HCVcc infection by the addition of purified recombinant protein. In contrast, while low concentrations of HCV E2 (0.05 μm) resulted in a similar level of inhibition, increasing HCV E2 concentrations clearly showed a dose dependent effect on HCVcc infection. Addition of 2 μm HCV E2 reduced the number of infected foci by 95%, strongly indicating that soluble HCV E2 specifically inhibits viral entry of HCVcc on Huh 7.5 cells.

Analysis of Secondary Structure of HCV E2

After confirming the functional properties of the recombinant *Drosophila*-produced sE2$_{715}$, which suggest that it has achieved a native conformation, the inventors set out to analyze the characteristics of its 3D fold more closely. The inventors carried out comparative circular dichroism analyses using class II proteins of known structure, the WNV sE (PDB 2HG0 and 2I69 [49, 50]) and the chikungunya virus (CHIK V) sE1. The latter is an alphavirus very close to Semliki Forest Virus, for which the structure of sE1 is known (PDB 2Ala [51, 52]).

The far-UV CD spectra of the three proteins exhibited considerable differences (FIG. 3A). However, after deconvolution to obtain the secondary structure composition of each protein (as described in the Methods' section), the percentage of secondary structure elements appears very similar for the three proteins, as indicated in the inset to FIG. 3A. Although each individual spectrum shows its minimum, maximum and baseline intercept at different wavelengths, the analysis indicated that all of them contain little α-helical secondary structure elements.

Far-UV CD is known to be very sensitive to the presence of α-helices, but less sensitive to β-sheet structures. The inventors therefore used Fourier Transform Infrared Spectroscopy (FTIR), which is more sensitive to β-sheet conformations, to complement the secondary structure analysis. FIG. 3B displays the high-frequency region of the FTIR spectra of soluble HCV E2 as well as Yellow Fever Virus sE or Dengue Virus 3 (DV3) protein used as a control. This spectral region contains the amide I band, which is particularly sensitive to the secondary structure of proteins. The main peak of the amide I band is observed for both proteins at 1630 cm−1, a position typical for β-sheet-containing polypeptides (reviewed in [53]). Both the CD and FTIR data indicate a considerable fraction of random-coil present in HCV sE2, as compared to the class II proteins used as control.

Disulfide Mapping Strategy

The inventors based the analysis of the disulfide connectivity pattern of HCV E2 on trypsin digestion of the soluble ectodomain sE2$_{715}$ under denaturing conditions and HPLC analysis of the resulting peptides, both under reducing and non-reducing conditions. The peaks in the elution chromatograms that were affected by reduction with TCEP (exemplified in FIG. 5A) were analyzed by N-terminal sequencing and mass spectrometry. In order to eliminate heterogeneity arising from the carbohydrate moiety, the proteins were fully deglycosylated using PNGase F in excess prior to this analysis.

As indicated in FIG. 4, the HCV sE2$_{715}$ sequences corresponding to the three isolates H77, JFH-1, UKN2b_2.8, display different patterns of predicted trypsin cleavage sites. The inventors used this difference to our advantage, to identify disulfide-linked peptides that could not be determined otherwise (e.g. disulfide bridge Cys581 to Cys585 was only identified in H77 E2 due to the lack of a trypsin cleavage site between Cys569 and Cys581). N-terminal sequencing of the selected peaks often resulted in identification of two amino acid stretches, which corresponded to two covalently linked peptides. But in many cases the inventors obtained only one single amino acid sequence, corresponding to a peptide having, in all cases, a pair number of cysteines (2 or 4) as well as at least one proline residue in between two proximal cysteines in the sequence, suggesting an intrapeptidic disulfide bridge spanning a turn in the amino acid backbone. A full list of the proteomics results is given in the supplemental material.

Determination of Disulfide Bridges in JFH-1 E2

In a first experiment the inventors performed a tryptic digestion of sE2$_{715}$ of the JFH-1 isolate (genbank accession GI:116078059). The HPLC chromatogram of the resulting digest revealed peaks 6-3, 12-3 and 16-3 to be TCEP sensitive and disappear upon reduction.

Peak 6-3 revealed a mixture of peptides, the N-terminal sequencing of which showed that only J1 and J2 (Table 1) contained a cysteine residue (position 452 and 459, respectively). In the respective mass spectrum a peak corresponding to the disulfide linked dipeptide could be identified (1471.71 Da), which disappeared upon reduction, indicating a disulfide bridge between Cys452 and Cys459.

Peak 12-3 contained peptides J6 and J7, each of which with one cysteine (position 607 and 644, respectively). While peptides J6 and J7 were found as single peptides in the mass spectrum, indicating partial reduction, the inventors also observed a peak at the predicted molecular weight of the two peptides linked by a disulfide bond (Fig. S1, 2045.37 Da). This peak disappeared, as expected, upon reduction. This clearly suggested a disulfide bridge between Cys607 and Cys644.

Peak 16-3 contained a mixture of peptides with one dominant sequence corresponding to peptide J4, containing two cysteines (position 503 and 508, respectively) and a praline residue in between. This peptide was unambiguously identified in the mass spectrum of peak 16-3 (FIG. 5B and Table 1, 2341.37 Da). Reduction with TCEP resulted in a molecular weight shift by 2 Da, which was interpreted two hydrogen atoms added upon reduction of the cysteines, demonstrating an intrapeptidic disulfide bridge between Cys503 and Cys508. Two more peptides, which could not be observed by mass spectrometry, were identified by N-terminal sequencing in peak 16-3: peptide J3 and peptide J5, containing Cys486 and 494 and Cys581 and 585, respectively.

Determination of Disulfide Bridges in UKN2b_2.8 E2

Subsequently the inventors subjected the sE2$_{715}$ from isolate UKN2b_2.8 to trypsin digestion. HPLC separation of the resulting peptides revealed that peaks 13-1, 20-1, 29-3, 42-3 and 19-1 were TCEP sensitive and disappeared upon reduction.

N-terminal sequencing identified two peptides, U6 and U7, containing Cys607 and Cys644, in peak 13-1 (which correspond to J6 and J7, see Table 1), confirming the data obtained with JFH-1 sE2$_{715}$. Mass spectrometry of U6 and U7 confirmed the presence of this disulfide bond in the UKN2b_2.8 isolate (2037.59 Da). However, the observed partial reduction of this disulfide bond in these strains suggested that experimentally induced disulfide shuffling may have occurred. In order to assess this, the inventors performed three different control experiments limiting this effect: (1) in-gel digestion in the presence of 5% DMSO, which acts as oxidizing agent, (2) digestion on a Nitrocellulose membrane in order to reduce incubation time to 3 h in the absence or (3) in the presence of NEM (N-ethylmaleimide), which covalently binds to free cysteines and thus blocks any disulfide rearrangements. The disulfide bridge between Cys607 and Cys644 was observed by N-terminal sequencing in all three control experiments (data not shown), strongly suggesting that it is also present in the native protein.

Peak 20-1 contained exclusively peptide U3, which corresponds to peptide J4 in JFH-1 $sE2_{715}$, thereby confirming the presence of a disulfide bridge between Cys503 and Cys508 (Table 1, 2194.94 Da).

Analysis of peak 29-3 revealed two TCEP sensitive peptides, U2 and U3. The inventors were identified U3 previously to carry an internal disulfide bridge, thus identifying an additional internal disulfide bond between Cys486 and Cys494 in peptide U2.

Peak 42-3 contained a mixture of three different peptides: U1, U3 and U4. Previous experiments showed that the two cysteines in U3 (Cys503 and Cys508) form an intrapeptidic disulfide bridge. Since U1 and U4 each contain one cysteine (position 429 and 552, respectively) this suggested a disulfide bond between Cys429 and Cys552. Although the disulfide linked peptides could not be identified by mass spectrometry, upon reduction a peak corresponding to the reduced peptide U1 was observed (Fig. S4, 2308 Da). Likely the high molecular weight of the disulfide linked dipeptide (U1+U4−6890.68 Da) prevented its appearance in the spectrum.

One peak (19-1) was found to contain a mixture of sequences, with one dominant sequence corresponding to peptide U5, in which two cysteines (position 581 and 585) are present. The inventors observed a peak corresponding to the peptide harboring an intrapeptidic disulfide bridge in the mass spectrum (Table 1, 1849.64 Da). Reduction resulted as expected in an increase of the molecular weight by 2 Da. In addition, peptide U2 was found in the same peak, which has previously been shown to carry an intrapeptidic disulfide bond.

Determination of Disulfide Bridges in H77 E2

Finally, the inventors performed a tryptic digestion of the of $sE2_{715}$ of H77 (genbank accession GI:130461) followed by HPLC of the resulting peptides, which revealed that peaks 15-2, 6-2, 26-2, 32-2, 43-2 and 33-2 disappeared upon reduction.

Peptides H5 and H6, which correspond to J6/J7 and U6/U7 were identified in peak 15-2. For both E2 of JFH-1 and UKN2b_2.8 a disulfide bridge between the respective cysteines (position 607 and 644) was shown in this study. Mass spectrometry clearly demonstrated the presence of a disulfide bridge between Cys607 and Cys644 in the ectodomain of H77 E2 as well (Table 1 and Fig. S5, 2110.35 Da).

Peptide H1 was found in two different peaks. Together with peptide H2, which corresponds to peptide J2, it was observed in peak 6-2, suggesting the presence of a disulfide bridge between Cys452 and Cys459, which has already been identified in $sE2_{715}$ from strain JFH-1. A peak in the mass spectrum corresponding to this peptide confirmed the presence of this disulfide bond (1544.29 Da). However, peptide H1 was also found together with peptide H6 in peak 26-2, which clearly suggested a disulfide rearrangement for these cysteines. In order to verify the actual disulfide bonding partner of Cys452 present in H1, the three control experiments mentioned above were performed. In all control experiments the disulfide bridge between peptides H1 and H2 was observed by N-terminal sequencing, while the presence of peptides H1 and H6 in the same peak disappeared under the control experiment conditions. Thus the inventors conclude that Cys452 is effectively linked to Cys459.

In peak 32-2 the inventors found only peptide H3, which corresponds to U2 (Table 1), in which the inventors were already identified an intrapeptidic disulfide bond. Mass spectrometry confirmed the presence of this disulfide bond between Cys486 and Cys494 (4321.98 Da).

Peak 43-2 consisted of the peptides H7 and H8, each containing one cysteine residue (position 652 and 677, respectively). In the mass spectrum the inventors observed a peak corresponding to the disulfide linked dipeptide (Table 1, 6849.91 Da), unambiguously identifying a disulfide bridge between Cys652 and Cys677 in the ectodomain of H77 E2.

Comparing the sequence alignment of E2 in the region between Cys569 and Cys581 the inventors noticed that while UKN2b_2.8 and JFH-1 E2 contain three trypsin cleavage sites, H77 E2 has no cleavage sites in this region (FIG. 4). Thus trypsin cleavage prediction in this region resulted in one peptide containing 4 cysteines, aligned sequentially in a way that the first two cysteines and the last two each have a proline residue in between. Analysis of peak 33-2 revealed only peptide H4, which corresponds to the predicted peptide containing 4 cysteines (positions 564, 569, 581 and 585, respectively). Mass spectrometry revealed a peak matching the predicted mass of this peptide containing two intrapeptidic disulfide bridges (2504.50 Da). Under non-reducing conditions two minor peaks could be observed, which are shifted by exactly 2 Da and thus likely correspond to partially reduced peptides in the original HPLC peak. Since the inventors were already identified the disulfide bond between Cys581 and Cys585 in UKN2b_2.8 E2, this result strongly indicates the presence of a disulfide bridge between Cys564 and Cys569.

Tryptic digestion followed by reverse-phase HPLC and further analysis of single peaks of the reverse phase HPLC by N-terminal sequencing and SELDI-TOF analysis allowed us to identify 8 out of 9 disulfide bridges present in HCV E2 (Table 2). 5 of them could be confirmed with different isolates.

Discussion

Figure 1:
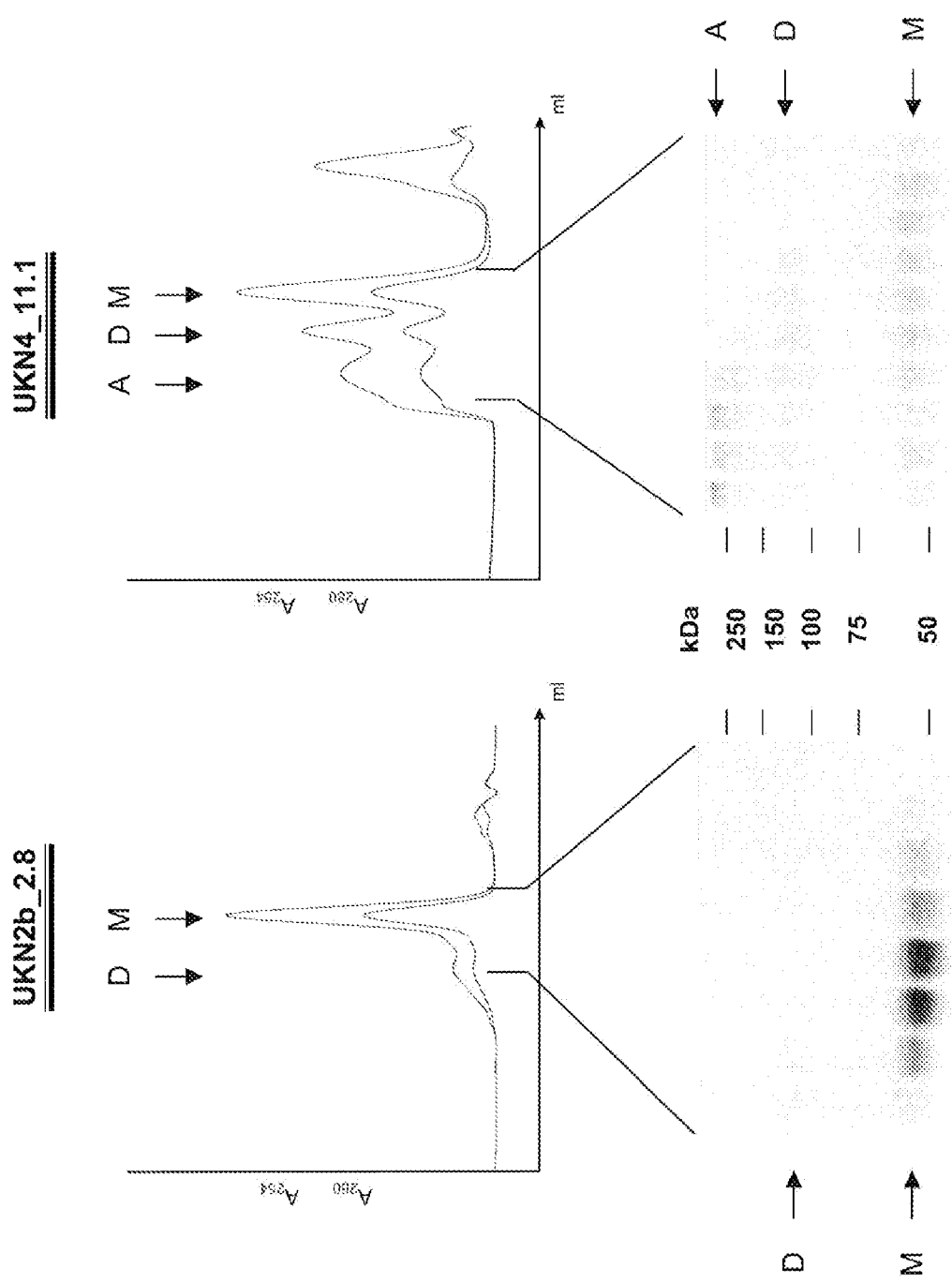
FIG. 1: Size exclusion chromatography of recombinant soluble HCV E2 expressed in *Drosophila* S2 cells Soluble E2 eluted from a Strep-Tactin column was separated in a size exclusion chromatography using a Superdex 200 column (GE Healthcare). Chromatograms showing absorption at 280 nm (top curve) and at 254 nm (bottom curve) as well as SDS-PAGE of corresponding fractions under non-reducing conditions followed by Coomassie staining are presented for isolates UKN2b_2.8 and UKN4_11.1, respectively. Arrows indicate aggregated (A), dimeric (D) and monomeric (M) forms of the protein.

Very little structural information is currently available on glycoprotein E2, a key player in Hepatitis C virus entry. E2 is the major viral antigen recognized by neutralizing antibodies in the infected organism and is also responsible for interactions with the cellular receptors SR-BI and CD81 during entry. Although many studies have provided important elements for understanding the HCV entry process, a detailed view of the molecular interactions is missing, in part due to the lack of structural information on the viral envelope proteins. Structural analyses of these proteins have been limited by the lack of purified samples in sufficient quantities, and the initial aim of this work was to develop a suitable protein production system of the HCV E2 glycoprotein for structural studies, taking advantage of the *Drosophila* S2 cell expression system. This system has been shown previously to result in the production of properly folded envelope glycoproteins for other members of the families Flaviviridae [54], Togaviridae [55], (Dubois et al., unpublished data), and of HIV gp120 [56], leading to the determination of the corresponding crystal structures. The advantage of the *Drosophila* system compared to others is that it is relatively easy to obtain stable transfectants (compared to mammalian cells) inducibly secreting the protein of interest without saturation of the chaperoning capacity of the ER (compared to the baculovirus infected lepidopteran cells). This is important for proteins with slow folding kinetics, as is the case for many of the viral class II membrane-fusogenic proteins, and which has also been shown for the HCV envelope proteins [57, 58]. Induced S2 cells remain healthy during a period of several weeks of recombinant protein secretion, without cell lysis which causes release of misfolded material into the medium—a problem with baculovirus infected insect cells, where lysis begins after about 3 days post-infection. Given that $sE2_{661}$ lacks the C-terminal cysteine (Cys677) the inventors decided to truncate our sE2 constructs at aa715, although previous studies reported inefficient folding and secretion of HCV $E2_{715}$ expressed in mammalian cells [43]. In our hands, the drosophila expressed recombinant HCV sE2 protein behaved as a soluble monomeric protein in gel filtration and did not form disulfide linked oligomeric aggregates, as observed previously with E2 made in different expression systems [43, 59] and remains monomeric at 4° C. for several months. The inventors found, however, that this quality of the fold of the secreted E2 protein depends on the used strain. For instance, sE2 from isolate UKN4_11.1 displayed a tendency to form disulfide-linked oligomers—which could however be separated from the monomeric form by size exclusion chromatography as shown in FIG. 1. This illustrates the effect that differences in the primary amino acid sequence—the isolates share more than 65% overall sequence identity—can exert on protein folding, even though the sequences of all used strains were shown to result in functionally competent envelope glycoproteins [46], validating our strategy of screening sE2 from a number of different strains in parallel. This is also reflected in the fact that quite variable overall yields of sE2 were obtained depending on the strain, again showing that some sequences behave better than others.

In order to ensure that the Drosophila expressed E2 proteins adopt a correct conformation, and therefore correct disulfide bonding pattern, the inventors selected isolates that had previously been shown to be functional in a HCVpp assay [46]. In addition, the inventors showed that the purified proteins were able to bind the large extracellular loop (LEL) of CD81 as well as two monoclonal conformation-sensitive anti-HCV E2 antibodies, which do not overlap with the CD81 binding site in HCV E2. This strongly suggests that the 3D fold—and therefore its disulfide connectivity pattern—is identical to the one present in E2 protein in virions. The functionality of our recombinant sE2 proteins was further confirmed by an in vivo assay, which demonstrated their capacity to compete with HCVcc for receptor binding and thus block infection of Huh-7.5 cells. The fact that sE2 efficiently inhibits HCVcc infection in a dose dependent way—in contrast to the effect of relevant controls like the soluble WNV E glycoprotein or the soluble pestiviral E2—strongly supports the notion that the recombinant HCV sE2 protein has acquired a functional conformation. Interestingly, previous studies failed to demonstrate effective reduction of infectivity using sE2 produced in a different expression system [48] and used at concentrations identical to some of the data points displayed in FIG. 2b. However this is likely due to the presence of incorrectly folded aggregates that are the hallmark of other sE2 constructs and expression systems [43, 59].

Disulfide bonds are key structural elements stabilizing the functional native conformation of viral envelope proteins. The inventors determined the disulfide connectivity pattern of HCV E2 by trypsin digestion followed by N-terminal sequencing and mass spectrometry. One disadvantage of this method is the occurrence of disulfide shuffling presumably taking place during trypsin digestion, which the inventors overcame by performing control experiments including N-ethylmaleimide whenever the results were ambiguous. The analysis was performed using recombinant E2 of three different strains representing two genotypes (1 and 2) and two subtypes of the latter, 2a and 2b. The ambiguities and difficulties in the identification of the peptides resulting from trypsin digestion of the different strains were different for each strain and gave complementary information, which together resulted in an unambiguous assessment. The inventors were thus able to experimentally identify eight disulfide bridges corresponding to 16 out of 18 cysteines. The last disulfide was therefore identified by exclusion, since the initial assumption is that the 18 strictly conserved cystein residues present in the HCV E2 ectodomain are all involved in disulfide bridges, as is the case in many other viral envelope proteins studied to date. Furthermore, five out of eight experimentally determined disulfide bridges were independently observed in more than one strain (Table 2). To the inventors knowledge this is the first report characterizing the disulfide connectivity pattern of a glycoprotein simultaneously for several strains of the same virus, experimentally confirming that the disulfide connectivity pattern and thus the overall three-dimensional fold of E2 is, as expected, strictly conserved within all genotypes of Hepatitis C virus.

The disulfide connectivity pattern strongly constrains the possible overall fold of the protein. The longer the distance along the primary structure between two cysteine residues forming a disulfide bridge, the stronger the impact for understanding the tertiary structure will be. In HCV E2 five out of nine disulfide bridges are formed by two consecutive cysteines, which are separated by less than 10 aa enclosing in each case one proline residue. The disulfide bridge connecting the two C-terminal cysteines and the two disulfide bridges Cys597-Cys620 as well as Cys 607-Cys644 span longer distances in the primary structure. In addition, there is one disulfide bridge (Cys429-Cys552) connecting the N-terminal with the C-terminal half of the protein, thus implying strong restraints on the overall fold of the protein.

The structural restraints implied by the disulfide connectivity pattern are not sufficient to clearly demonstrate a particular fold of the HCV E2 ectodomain, thus a number of different overall protein folds would be conceivable. All of these need to combine the disulfide connectivity pattern determined in this study with the results of the secondary structure analysis of HCV E2 as well as a previously suggested composite CD81 binding platform [14-17]. One possible fold of HCV E2 predominantly consisting of beta sheets, which possess the determined disulfide pattern and contains a composite CD81 binding site is shown in FIG. 6.

However, the present experimental observation by circular dichroism and Fourier-Transform Infra-Red spectroscopy that HCV E2 consists mainly of beta sheets, could also be interpreted to further support the hypothesis that its fold is belongs to the class II fold observed in the related flaviviruses. The hall mark of the latter is the presence of a central domain ("domain I") folded as a beta barrel with up-and-down topology, flanked on each side by two other beta-rich domains [60]. Two long loops (insertions) connecting sequential strands in domain one ($D_0$-$E_0$ and $H_0$-$I_0$ loops) form the complex "domain II", with the fusion loop at the tip; domain III, which has an Ig-like fold, is connected via a flexible linker to the opposite side of domain I, following strand $I_0$.

The disulfide connectivity of HCV E2 is consistent with such a fold only if the inventors assume that the second loop forming domain II ($H_0$-$I_0$ loop) is absent, or is very short. There are a number of possibilities to arrange the polypeptide chain to conform to both, a class II fold and the constraints introduced by the disulfide bonding pattern. The inventors present in FIG. 6 one possible arrangement, which takes into account additional conformational data, in particular, the location of N-glycosylation sites and of residues that affect binding to CD81.

In flaviviruses, domain I contains an N-terminal extension, which includes strand $A_0$ (absent in the alphaviruses). In HCV E2, the N-terminal region is variable (termed "hypervariable region 1" (HVR1)) and has been shown not to be essential for the folding of E2. Deletions mutants in which the HVR1 is absent appear to fold correctly and to be infectious in HCVpp assays [61], suggesting that this region is also an N-terminal extension of domain I. The HVR1 extends to about residue 410 [62], indicating that the N-terminus of domain I would begin roughly at this position. Besides the HVR1 two more variable regions are described in HCV E2, the "hypervariable region 2" (HVR2), located within Cys459 and Cys486 (residues 474-482, [63]), and the intergenotypic variable region (IgVR) located within Cys 569 and Cys 581 [64]. A core domain of HCV E2 has been described lacking all three variable regions [64] based on the assumption that the cysteines flanking HVR2 and IgVR are disulfide bonded and the protein would attain its global fold in spite of the deletion of these loops, as in the case of HIV gp120 [56]. However, although in contrast to the surface loops in gp120 the cysteines flanking HVR2 and IgVR are not disulfide bonded, as assumed by the authors, such a deletion mutant still appears to fold and retains a functional conformation as attested by the binding of CD81 or antibodies recognizing conformational epitopes [64]. This observation suggests that the region containing the HVR2, representing a part of domain II (in yellow in FIG. 6) is not rigidly structured—at least in the absence of E1—and maybe structure by contacts in the heterodimer at the virion surface, and that this region folds independently of domain I. It has been shown previously that CD81 binding, which according to our model predominantly occurs in domain I, is maintained, while recognition by conformation-dependent monoclonal antibodies can be impaired [32].

The third variable region, the IgVR represents a variable linker between domain I and domain III, which displays a polymorphism of linker length in different HCV strains and isolates, thus suggesting that removal of this region would not impair overall protein fold or function. In class II fusion proteins, this linker region between domains I and III, becomes stretched after the conformational change to allow DII to reach a position on the side of the post-fusion class II homotrimer.

In the prefusion form of flavi- and alphaviruses envelope proteins one side of each domain I and domain III are juxtaposed [51, 60]. The presented model of HCV E2 contains two of the three discontinuous regions of the polypeptide forming the CD81 binding interface [14-17] located in domain I, the third one in domain III, the three of them forming a binding site crossing the interface between these two domains.

The mechanism of membrane fusion induced by the HCV glycoproteins and the identity of the fusion loop has been subject of several studies spanning both glycoproteins E1 and E2 [28,29,65]. In the flavi- and alphaviruses the fusion loop is located in domain II. The determined disulfide connectivity pattern provides little information about this region, containing only three disulfide bridges formed by consecutive cysteines. Two regions have been proposed previously in E2 to act as fusion determinants (416-430 and 600-620) [29]. Due to their location within the receptor binding interface of the E2 molecule, which is likely an exposed platform in order to facilitate binding to CD81, both of these regions have been placed in domain I and domain III, respectively, suggesting that the identity of the fusion loop remains to be elucidated. The structural information available to date, in particular with respect to domain II, does not allow its identification, but will be highly useful to design further experiments.

The N-glycosylation sites in E2 are located exclusively on the outward-facing surface of the molecule or in the connecting regions between the beta strands thus allowing the placement of E2 flat onto the viral membrane as shown for flavivirus E protein [66]. It has been shown previously that mutation of single N-glycosylation sites reduces entry of HCVpp without affecting the overall fold of HCV E2 by modulating binding to CD81 [32, 67], indicating a close proximity between these N-linked carbohydrates and the CD81 binding site. The N-glycosylation sites N1 (N417) and N6 (N532) are reported to increase the affinity to CD81 and N11 have been shown to modulate entry of HCVpp [67, 68]. All of these N-glycosylation sites are located close to the proposed CD81 binding site, thus explaining the modified HCVpp entry.

The combination of MS and N-terminal sequencing of peptide fragments has allowed the inventors to assign all disulfide bonds in HCV E2. Based on this knowledge and the secondary structure analysis of the HCV E2 ectodomain the inventors propose an overall fold that is consistant with HCV E2 being a class II viral fusion protein. This model enlarges understanding of receptor binding as well as glycoprotein interactions and other putative functions of HCV E2 during viral entry and will be highly useful for design of new experiments. One important implication is that the residues interacting with CD81 are found in two domains, domain I and domain III, which have to move apart during the fusogenic conformational change. This suggest that CD81 may have to dissociate away for such a conformational change to take place, or on the contrary, that its binding may help to lower the energy barrier for the conformational change to occur upon exposure to low pH in the endosomes.

REFERENCES

1. Yagnik A T, Lahm A, Meola A, Roccasecca R M, Ercole B B, et al. (2000) A model for the hepatitis C virus envelope glycoprotein E2. Proteins 40: 355-366.
2. Lindenbach B D, Thiel H J, Rice C M (2007) Flaviviridae: The viruses and their replication. Fields Virology, Fifth edition: 1101-1152.
3. Penin F, Dubuisson J, Rey F A, Moradpour D, Pawlotsky J M (2004) Structural biology of hepatitis C virus. Hepatology 39: 5-19.
4. Andre P, Perlemuter G, Budkowska A, Brechot C, Lotteau V (2005) Hepatitis C virus particles and lipoprotein metabolism. Semin Liver Dis 25: 93-104.
5. Pileri P, Uematsu Y, Campagnoli S, Galli G, Falugi F, et al. (1998) Binding of hepatitis C virus to CD81. Science 282: 938-941.
6. Evans M J, von Hahn T, Tscherne D M, Syder A J, Panis M, et al. (2007) Claudin-1 is a hepatitis C virus co-receptor required for a late step in entry. Nature 446: 801-805.
7. Meertens L, Bertaux C, Cukierman L, Cormier E, Lavillette D, et al. (2008) The tight junction proteins claudin-1, -6, and -9 are entry cofactors for hepatitis C virus. J Virol 82: 3555-3560.
8. Ploss A, Evans M J, Gaysinskaya V A, Panis M, You H, et al. (2009) Human occludin is a hepatitis C virus entry factor required for infection of mouse cells. Nature.
9. Scarselli E, Ansuini H, Cerino R, Roccasecca R M, Acali S, et al. (2002) The human scavenger receptor class B type I is a novel candidate receptor for the hepatitis C virus. Embo J 21: 5017-5025.

10. Monazahian M, Bohme I, Bonk S, Koch A, Scholz C, et al. (1999) Low density lipoprotein receptor as a candidate receptor for hepatitis C virus. J Med Virol 57: 223-229.
11. Koutsoudakis G, Kaul A, Steinmann E, Kallis S, Lohmann V, et al. (2006) Characterization of the early steps of hepatitis C virus infection by using luciferase reporter viruses. J Virol 80: 5308-5320.
12. Zeisel M B, Koutsoudakis G, Schnober E K, Haberstroh A, Blum H E, et al. (2007) Scavenger receptor class B type I is a key host factor for hepatitis C virus infection required for an entry step closely linked to CD81. Hepatology 46: 1722-1731.
13. Callens N, Ciczora Y, Bartosch B, Vu-Dac N, Cosset F L, et al. (2005) Basic residues in hypervariable region 1 of hepatitis C virus envelope glycoprotein e2 contribute to virus entry. J Virol 79: 15331-15341.
14. Drummer H E, Boo I, Maerz A L, Poumbourios P (2006) A conserved Gly436-Trp-Leu-Ala-Gly-Leu-Phe-Tyr motif in hepatitis C virus glycoprotein E2 is a determinant of CD81 binding and viral entry. J Virol 80: 7844-7853.
15. Keck Z Y, Olson O, Gal-Tanamy M, Xia J, Patel A H, et al. (2008) A point mutation leading to hepatitis C virus escape from neutralization by a monoclonal antibody to a conserved conformational epitope. J Virol 82: 6067-6072.
16. Owsianka A M, Timms J M, Tarr A W, Brown R J, Hickling T P, et al. (2006) Identification of conserved residues in the E2 envelope glycoprotein of the hepatitis C virus that are critical for CD81 binding. J Virol 80: 8695-8704.
17. Rothwangl K B, Manicassamy B, Uprichard S L, Rong L (2008) Dissecting the role of putative CD81 binding regions of E2 in mediating HCV entry: putative CD81 binding region 1 is not involved in CD81 binding. Virol J 5: 46.
18. Kapadia S B, Barth H, Baumert T, McKeating J A, Chisari F V (2007) Initiation of hepatitis C virus infection is dependent on cholesterol and cooperativity between CD81 and scavenger receptor B type I. J Virol 81: 374-383.
19. Blanchard E, Belouzard S, Goueslain L, Wakita T, Dubuisson J, et al. (2006) Hepatitis C virus entry depends on clathrin-mediated endocytosis. J Virol 80: 6964-6972.
20. Tscherne D M, Jones C T, Evans M J, Lindenbach B D, McKeating J A, et al. (2006) Time- and temperature-dependent activation of hepatitis C virus for low-pH-triggered entry. J Virol 80: 1734-1741.
21. Andersson H, Barth B U, Ekstrom M, Garoff H (1997) Oligomerization-dependent folding of the membrane fusion protein of Semliki Forest virus. J Virol 71: 9654-9663.
22. Lorenz I C, Allison S L, Heinz F X, Helenius A (2002) Folding and dimerization of tick-borne encephalitis virus envelope proteins prM and E in the endoplasmic reticulum. J Virol 76: 5480-5491.
23. Bressanelli S, Stiasny K, Allison S L, Stura E A, Duqueroy S, et al. (2004) Structure of a flavivirus envelope glycoprotein in its low-pH-induced membrane fusion conformation. Embo J 23: 728-738.
24. Modis Y, Ogata S, Clements D, Harrison S C (2004) Structure of the dengue virus envelope protein after membrane fusion. Nature 427: 313-319.
25. Gibbons D L, Vaney M C, Roussel A, Vigouroux A, Reilly B, et al. (2004) Conformational change and protein-protein interactions of the fusion protein of Semliki Forest virus. Nature 427: 320-325.
26. Kielian M, Rey F A (2006) Virus membrane-fusion proteins: more than one way to make a hairpin. Nat Rev Microbiol 4: 67-76.
27. Yu X, Qiao M, Atanasov I, Hu Z, Kato T, et al. (2007) Cryo-electron microscopy and three-dimensional reconstructions of hepatitis C virus particles. Virology 367: 126-134.
28. Lavillette D, Bartosch B, Nourrisson D, Verney G, Cosset F L, et al. (2006) Hepatitis C virus glycoproteins mediate low pH-dependent membrane fusion with liposomes. J Biol Chem 281: 3909-3917.
29. Lavillette D, Pecheur E I, Donot P, Fresquet J, Molle J, et al. (2007) Characterization of fusion determinants points to the involvement of three discrete regions of both E1 and E2 glycoproteins in the membrane fusion process of hepatitis C virus. J Virol 81: 8752-8765.
30. Perez-Berna A J, Moreno M R, Guillen J, Bernabeu A, Villalain J (2006) The membrane-active regions of the hepatitis C virus E1 and E2 envelope glycoproteins. Biochemistry 45: 3755-3768.
31. Goffard A, Dubuisson J (2003) Glycosylation of hepatitis C virus envelope proteins. Biochimie 85: 295-301.
32. Goffard A, Callens N, Bartosch B, Wychowski C, Cosset F L, et al. (2005) Role of N-linked glycans in the functions of hepatitis C virus envelope glycoproteins. J Virol 79: 8400-8409.
33. Blight K J, McKeating J A, Rice C M (2002) Highly permissive cell lines for subgenomic and genomic hepatitis C virus RNA replication. J Virol 76: 13001-13014.
34. De Tomassi A, Pizzuti M, Graziani R, Sbardellati A, Altamura S, et al. (2002) Cell clones selected from the Huh7 human hepatoma cell line support efficient replication of a subgenomic GB virus B replicon. J Virol 76: 7736-7746.
35. Wakita T, Pietschmann T, Kato T, Date T, Miyamoto M, et al. (2005) Production of infectious hepatitis C virus in tissue culture from a cloned viral genome. Nat Med 11: 791-796.
36. Kitadokoro K, Galli G, Petracca R, Falugi F, Grandi G, et al. (2001) Crystallization and preliminary crystallographic studies on the large extracellular domain of human CD81, a tetraspanin receptor for hepatitis C virus. Acta Crystallogr D Biol Crystallogr 57: 156-158.
37. Whitmore L, Wallace B A (2004) DICHROWEB, an online server for protein secondary structure analyses from circular dichroism spectroscopic data. Nucleic Acids Res 32: W668-673,
38. Whitmore L, Wallace B A (2008) Protein secondary structure analyses from circular dichroism spectroscopy: methods and reference databases. Biopolymers 89: 392-400.
39. Lees J G, Miles A J, Wien F, Wallace B A (2006) A reference database for circular dichroism spectroscopy covering fold and secondary structure space. Bioinformatics 22: 1955-1962.
40. Baker P R, Clauser K R http://prospector.ucsf.edu.
41. Wilkins M R, Lindskog I, Gasteiger E, Bairoch A, Sanchez J C, et al. (1997) Detailed peptide characterization using PEPTIDEMASS—a World-Wide-Web-accessible tool. Electrophoresis 18: 403-408.
42. Hosfield T, Lu Q (1999) Influence of the amino acid residue downstream of (Asp)4Lys on enterokinase cleavage of a fusion protein. Anal Biochem 269: 10-16.
43. Michalak J P, Wychowski C, Choukhi A, Meunier J C, Ung S, et al. (1997) Characterization of truncated forms of hepatitis C virus glycoproteins. J Gen Virol 78 (Pt 9): 2299-2306.
44. Owsianka A, Clayton R F, Loomis-Price L D, McKeating J A, Patel A H (2001) Functional analysis of hepatitis C virus E2 glycoproteins and virus-like particles reveals structural dissimilarities between different forms of E2. J Gen Virol 82: 1877-1883.

45. Brazzoli M, Helenius A, Foung S K, Houghton M, Abrignani S, et al. (2005) Folding and dimerization of hepatitis C virus E1 and E2 glycoproteins in stably transfected CHO cells. Virology 332: 438-453.

46. Lavillette D, Tarr A W, Voisset C, Donot P, Bartosch B, et al. (2005) Characterization of host-range and cell entry properties of the major genotypes and subtypes of hepatitis C virus. Hepatology 41: 265-274.

47. Keck Z Y, Op De Beeck A, Hadlock K G, Xia J, Li T K, et al. (2004) Hepatitis C virus E2 has three immunogenic domains containing conformational epitopes with distinct properties and biological functions. J Viral 78: 9224-9232.

48. Harris H J, Farquhar M J, Mee C J, Davis C, Reynolds G M, et al. (2008) CD81 and claudin 1 coreceptor association: role in hepatitis C virus entry. J Virol 82: 5007-5020.

49. Kanai R, Kar K, Anthony K, Gould L H, Ledizet M, et al. (2006) Crystal structure of west nile virus envelope glycoprotein reveals viral surface epitopes. J Viral 80: 11000-11008.

50. Nybakken G E, Nelson C A, Chen B R, Diamond M S, Fremont D H (2006) Crystal structure of the West Nile virus envelope glycoprotein. J Viral 80: 11467-11474.

51. Lescar J, Roussel A, Wien M W, Navaza J, Fuller S D, et al. (2001) The Fusion glycoprotein shell of Semliki Forest virus: an icosahedral assembly primed for fusogenic activation at endosomal pH. Cell 105: 137-148.

52. Roussel A, Lescar J, Vaney M C, Wengler G, Wengler G, et al. (2006) Structure and interactions at the viral surface of the envelope protein E1 of Semliki Forest virus. Structure 14: 75-86.

53. Goormaghtigh E, Cabiaux V, Ruysschaert J M (1994) Determination of soluble and membrane protein structure by Fourier transform infrared spectroscopy. I. Assignments and model compounds. Subcell Biochem 23: 329-362.

54. Modis Y, Ogata S, Clements D, Harrison S C (2003) A ligand-binding pocket in the dengue virus envelope glycoprotein. Proc Natl Acad Sci USA 100: 6986-6991

55. Umashankar M, Sanchez-San Martin C, Liao M, Reilly B, Guo A, et al. (2008) Differential cholesterol binding by class II fusion proteins determines membrane fusion properties. J Virol 82: 9245-9253.

56. Kwong P D, Wyatt R, Robinson J, Sweet R W, Sodroski J, et al. (1998) Structure of an HIV gp120 envelope glycoprotein in complex with the CD4 receptor and a neutralizing human antibody. Nature 393: 648-659.

57. Dubuisson J, Rice C M (1996) Hepatitis C virus glycoprotein folding: disulfide bond formation and association with calnexin. J Virol 70: 778-786.

58. Merola M, Brazzoli M, Cocchiarella F, Heile J M, Helenius A, et al. (2001) Folding of hepatitis C virus E1 glycoprotein in a cell-free system. J Virol 75: 11205-11217.

59. Dubuisson J, Hsu H H, Cheung R C, Greenberg H B, Russell D G, et al. (1994) Formation and intracellular localization of hepatitis C virus envelope glycoprotein complexes expressed by recombinant vaccinia and Sindbis viruses. J Virol 68: 6147-6160.

60. Rey F A, Heinz F X, Mandl C, Kunz C, Harrison S C (1995) The envelope glycoprotein from tick-borne encephalitis virus at 2 A resolution. Nature 375: 291-298.

61. Bartosch B, Verney G, Dreux M, Donot P, Morice Y, et al. (2005) An interplay between hypervariable region 1 of the hepatitis C virus E2 glycoprotein, the scavenger receptor BI, and high-density lipoprotein promotes both enhancement of infection and protection against neutralizing antibodies. J Virol 79: 8217-8229.

62. Weiner A J, Brauer M J, Rosenblatt J, Richman K H, Tung J, et al. (1991) Variable and hypervariable domains are found in the regions of HCV corresponding to the flavivirus envelope and NS1 proteins and the pestivirus envelope glycoproteins. Virology 180: 842-848.

63. Kato N, Ootsuyama Y, Ohkoshi S, Nakazawa T, Sekiya H, et al. (1992) Characterization of hypervariable regions in the putative envelope protein of hepatitis C virus. Biochem Biophys Res Commun 189: 119-127.

64. McCaffrey K, Boo I, Poumbourios P, Drummer H E (2007) Expression and characterization of a minimal hepatitis C virus glycoprotein E2 core domain that retains CD81 binding. J Virol 81: 9584-9590.

65. Drummer H E, Boo I, Poumbourios P (2007) Mutagenesis of a conserved fusion peptide-like motif and membrane-proximal heptad-repeat region of hepatitis C virus glycoprotein E1. J Gen Virol 88: 1144-1148.

66. Kuhn R J, Zhang W, Rossmann M G, Pletnev S V, Carver J, et al. (2002) Structure of dengue virus: implications for flavivirus organization, maturation, and fusion. Cell 108: 717-725.

67. Falkowska E, Kajumo F, Garcia E, Reinus J, Dragic T (2007) Hepatitis C virus envelope glycoprotein E2 glycans modulate entry, CD81 binding, and neutralization. J Virol 81: 8072-8079.

68. Nelle F, Goffard A, Morel V, Duverlie G, McKeating J, et al. (2007) The neutralizing activity of anti-hepatitis C virus antibodies is modulated by specific glycans on the E2 envelope protein. J Virol 81: 8101-8111.

TABLE 1

Identification of disulfide containing HCV E2 peptides resulting from tryptic digestion.

| peptide | Amino acid sequence | predicted mass | determined mass |
|---------|---------------------|----------------|-----------------|
| JFH-1 | | | |
| J1 | FDSSGC$_{452}$PGR | 925.9911 | n.f. |
| J2 | LSAC$_{459}$R | 549.6654 | n.f. |
| J3 | IGWGTLQYEDDVTNPEDMRPYC$_{486}$WHYPPKPC$_{494}$GVVPAR | 4192.7303 | n.f. |
| J4 | SVC$_{503}$GPVYC$_{508}$FTPSPVVVGTTDRR | 2341.7051 | 2341.37 |
| J5 | ADFDASTDLLC$_{581}$PTDC$_{585}$FR | 1891.0769 | n.f. |
| J6 | C$_{607}$LVHYPYR | 1051.2508 | 1050.63 |
| J7 | LTAAC$_{644}$NFTR | 998.1414 | 998.05 |
| disulfide linked peptides | | | |
| J1 + J2 | | 1472.6515 | 1471.71 |

TABLE 1-continued

Identification of disulfide containing HCV E2 peptides resulting from tryptic digestion.

| peptide | Amino acid sequence | predicted mass | determined mass |
|---|---|---|---|
| | J3 | 4190.7569 | n.f. |
| | J4 | 2339.7141 | 2339.30 |
| | J5 | 1889.0822 | n.f. |
| | J6 + J7 | 2046.3921 | 2045.37 |
| UKN2b_2.8 | | | |
| U1 | TALNC$_{429}$DDSLQTGFLASLFYVK | 2307.6228 | 2308.00 |
| U2 | IGWGTLEYETDATNDEDMRPYC$_{486}$WHYPPRPC$_{494}$GIVSAR | 4201.6514 | n.f. |
| U3 | TVC$_{503}$GPVYC$_{508}$FTPSPVVVGTTDR | 2199.5445 | 2195.75 |
| U4 | QGVPTYSWGEDETDVFLLDSTRPPQGAWFGC$_{552}$TWMDGTGFT | 4586.0192 | n.f. |
| U5 | DHDSTLDLLC$_{581}$PTDC$_{585}$FR | 1852.0432 | 1851.50 |
| U6 | C$_{607}$LVDYPYR | 1029.1983 | 1028.80 |
| U7 | LNAAC$_{644}$DFTR | 1011.1401 | 1010.87 |
| | disulfide linked peptides | | |
| | U1 + U4 | 6890.6802 | n.f. |
| | U2 | 4199.6775 | n.f. |
| | U3 | 2197.5525 | 2194.94 |
| | U5 | 1850.0483 | 1849.64 |
| | U6 + U7 | 2037.338 | 2037.59 |
| H77 | | | |
| H1 | FDSSGC$_{452}$PER | 998.0547 | n.f. |
| H2 | LASC$_{459}$R | 549.6654 | n.f. |
| H3 | LTDFAQGWGPISYADGSGLDERPYC$_{486}$WHYPPRPC$_{494}$GIVPAK | 4322.8613 | n.f. |
| H4 | VC$_{564}$GAPPC$_{569}$VIGGVGDNTLLC$_{581}$PTDC$_{585}$FR | 2508.9457 | 2508.81 |
| H5 | C$_{607}$MVDYPYR | 1047.2315 | n.f. |
| H6 | LEAAC$_{644}$DWTR | 1065.1884 | 1065.98 |
| H7 | C$_{652}$DLEDRDR | 750.8011 | n.f. |
| H8 | SELSPLLLSTTQWQVLPC$_{677}$SF . . . SSIASWAIK | 6100.0588 | n.f. |
| | disulfide linked peptides | | |
| | H1 + H2 | 1544.715 | 1544.29 |
| | H3 | 4320.8851 | 4321.98 |
| | H4 | 2504.9486 | 2504.50 |
| | H5 + H6 | 2109.4239 | 2110.35 |
| | H7 + H8 | 6847.8954 | 6849.91 |

Peptides resulting from tryptic digestion of soluble E2 from three different isolates were identified by N-terminal sequencing and mass spectrometry (n.f.—not found in mass spectrometry). Peptides were named according to the isolate and numbered sequentially according to their appearance in the full ectodomain amino acid sequence. Molecular mass predictions were performed using MS-BRIDGE [40] for disulfide-connected peptides and using PeptideMass for reduced peptides [41].

| Peptide | SEQ ID NO: |
|---|---|
| FDSSGC$_{452}$PGR | 20 |
| LSAC$_{459}$R | 21 |
| IGWGTLQYEDDVTNPEDMRPYC$_{486}$WHYPPKPC$_{494}$GVVPAR | 22 |
| SVC$_{503}$GPVYC$_{508}$FTPSPVVVGTTDRR | 23 |
| ADFDASTDLLC$_{581}$PTDC$_{585}$FR | 24 |
| C$_{607}$LVHYPYR | 25 |
| LTAAC$_{644}$NFTR | 26 |
| TALNC$_{429}$DDSLQTGFLASLFYVK | 27 |
| IGWGTLEYETDATNDEDMRPYC$_{486}$WHYPPRPC$_{494}$GIVSAR | 28 |
| TVC$_{503}$GPVYC$_{506}$FTPSPVVVGTTDR | 29 |
| QGVPTYSWGEDETDVFLLDSTRPPQGAWFGC$_{552}$TWMDGTGFT | 30 |
| DHDSTLDLLC$_{581}$PTDC$_{585}$FR | 31 |
| C$_{607}$LVDYPYR | 32 |
| LNAAC$_{644}$DFTR | 33 |
| FDSSGC$_{452}$PER | 34 |
| LASC$_{459}$R | 35 |
| LTDFAQGWGPISYADGSGLDERPYC$_{486}$WHYPPRPC$_{494}$GIVPAK | 36 |
| VC$_{564}$GAPPC$_{569}$VIGGVGDNTLLC$_{581}$PTDC$_{585}$FR | 37 |
| C$_{607}$MVDYPYR | 38 |

| Peptide | SEQ ID NO: |
|---|---|
| LEAAC$_{644}$DWTR | 39 |
| C$_{652}$DLEDRDR | 40 |
| SELSPLLLSTTQWQVLPC$_{677}$SF . . . SSIASWAIK | 41 |

TABLE 2

|  | H77 | JFH-1 | UKN2b_2.8 |
|---|---|---|---|
| Cys429-Cys552 |  |  | + |
| Cys452-Cys459 | + | + |  |
| Cys486-Cys494 | + | + | + |
| Cys503-Cys508 |  | + | + |
| Cys564-Cys569 | + |  |  |
| Cys581-Cys585 (Cys597-Cys620) | + | + | + |
| Cys607-Cys644 | + | + | + |
| Cys652-Cys677 | + |  |  |

The invention claimed is:

1. An isolated polypeptide comprising a peptide selected from the group consisting of:
   (a) a peptide comprising at least 95% identity to SEQ ID NO: 1; and
   (b) a peptide comprising or consisting of SEQ ID NO: 1.

2. A pharmaceutical composition comprising an isolated polypeptide and a pharmaceutically acceptable carrier, wherein the isolated polypeptide comprises a peptide selected from the group consisting of:
   (a) a peptide comprising at least 95% identity to SEQ ID NO: 1; and
   (b) a peptide comprising or consisting of SEQ ID NO: 1.

3. A method for treating a Hepatitis C virus (HCV) infection in a host, comprising administering to said host a therapeutically effective quantity of a polypeptide according to claim 1.

4. The method according to claim 3, wherein the host is an animal.

5. The method according to claim 3, wherein the host is a human.

6. A Kit comprising a polypeptide according to claim 1 for detection or diagnosis of HCV infection.

* * * * *